(12) United States Patent
Seligman

(10) Patent No.: US 12,740,780 B2
(45) Date of Patent: Sep. 22, 2026

(54) GRIP FOR A NEEDLE DRIVER AND METHODS OF MANUFACTURE AND USE THEREOF

(71) Applicant: Ergosurgical Group Corp., Santa Maria, PR (US)

(72) Inventor: Scott Seligman, San Marcos, CA (US)

(73) Assignee: Ergosurgical Group Corp., PR (US)

( * ) Notice: Subject to any disclaimer, the term of this patent is extended or adjusted under 35 U.S.C. 154(b) by 0 days.

(21) Appl. No.: 18/820,066

(22) Filed: Aug. 29, 2024

(65) Prior Publication Data

US 2025/0072885 A1 Mar. 6, 2025

Related U.S. Application Data

(60) Provisional application No. 63/535,261, filed on Aug. 29, 2023.

(51) Int. Cl.
*A61B 17/04* (2006.01)
*A61B 17/062* (2006.01)
*A61B 17/29* (2006.01)

(52) U.S. Cl.
CPC ...... *A61B 17/0469* (2013.01); *A61B 17/0491* (2013.01); *A61B 17/062* (2013.01); *A61B 17/2909* (2013.01)

(58) Field of Classification Search
CPC .............. A61B 17/0469; A61B 17/062; A61B 17/0483; A61B 17/0491; A61B 17/06;
(Continued)

(56) References Cited

U.S. PATENT DOCUMENTS 1,108,737 A 8/1914 Gajdos
2,601,564 A 6/1952 Smith
(Continued)

FOREIGN PATENT DOCUMENTS

CN 115153698 10/2022
WO WO2009039506 3/2009
(Continued)

OTHER PUBLICATIONS

Fontanelli et al., A New Laparoscopic Tool with In-Hand Rolling Capabilities for Needle Reorientation, IEE Robotics and Automation Letters, Jan. 2018 (8 pages).
(Continued)

*Primary Examiner* — Majid Jamialahmadi
(74) *Attorney, Agent, or Firm* — Dentons US LLP

(57) ABSTRACT

An improved grip for a needle driver is disclosed. The grip includes an upper jaw including an upper roller and a lower jaw including a lower roller, and includes a guard that is distributed across the jaws that prevents a needle and/or suture from entering a non-grasping portion of the grip. The grip also includes a shifting feature that is distributed across at least one of the jaws and at least one of the rollers. The shifting feature increasingly “shifts” or moves one of the rollers in a longitudinal direction towards a distal end of the needle driver, while the other roller remains stationary, until the shifting roller overlaps the stationary roller, and peaks of the shifting roller are seated within valleys of the stationary roller, thus grasping the suture between the rollers. The grip also drives a needle between the rollers when the grip is in a driving position.

32 Claims, 11 Drawing Sheets

(58) Field of Classification Search
CPC .......... A61B 17/06066; A61B 17/0482; A61B 34/30; A61B 2034/305; A61B 2017/0472; A61B 2017/2923; A61B 2017/2932; A61B 2017/2943
See application file for complete search history.

(56) References Cited

U.S. PATENT DOCUMENTS 3,168,097 A 2/1965 Earico
4,452,244 A 6/1984 Chin
4,580,567 A 4/1986 Schweitzer et al.
4,635,638 A 1/1987 Weintraub et al.
4,763,669 A 8/1988 Jaeger
5,496,334 A 3/1996 Klundt et al.
5,501,690 A 3/1996 Measamer et al.
5,582,617 A 12/1996 Klieman et al.
5,628,757 A 5/1997 Hasson
5,632,432 A 5/1997 Schulze
5,649,955 A 7/1997 Hashimoto
5,759,188 A 6/1998 Yoon
5,843,100 A 12/1998 Meade
5,860,992 A 1/1999 Daniel et al.
5,891,159 A 4/1999 Sherman et al.
5,897,563 A 4/1999 Yoon et al.
5,954,731 A 9/1999 Yoon
5,954,733 A 9/1999 Yoon
5,957,937 A 9/1999 Yoon
5,984,932 A 11/1999 Yoon
5,993,466 A 11/1999 Yoon
5,993,467 A 11/1999 Yoon
6,004,332 A 12/1999 Yoon et al.
6,071,289 A 6/2000 Stefanchik et al.
6,086,601 A 7/2000 Yoon
6,126,665 A 10/2000 Yoon
6,143,005 A 11/2000 Yoon et al.
6,159,224 A 12/2000 Yoon
6,224,614 B1 5/2001 Yoon
7,331,970 B2 2/2008 Almodovar
7,588,583 B2 9/2009 Hamilton et al.
8,021,376 B2 9/2011 Takemoto et al.
8,252,007 B2 8/2012 Hamilton et al.
8,317,805 B2 11/2012 Hamilton et al.
8,603,113 B2 12/2013 Hamilton et al.
8,696,690 B2 4/2014 Almodovar
9,192,376 B2 11/2015 Almodovar
9,730,689 B2 8/2017 Almodovar
10,786,245 B2 9/2020 Almodovar
10,786,272 B2 9/2020 Beira
11,439,397 B2 9/2022 Smith
2003/0181924 A1 9/2003 Yamamoto et al.
2006/0020272 A1 1/2006 Gildenberg
2006/0064116 A1 3/2006 Allen et al.
2006/0282096 A1 12/2006 Papa et al.
2007/0016287 A1 1/2007 Cartledge et al.
2007/0021755 A1 1/2007 Almodovar
2007/0135913 A1 6/2007 Moaddeb et al.
2007/0203507 A1 8/2007 McLaughlin et al.
2008/0004604 A1 1/2008 Hartwick
2008/0071295 A1 3/2008 Baxter et al.
2008/0103511 A1 5/2008 Almodovar
2008/0262609 A1 10/2008 Gross et al.
2009/0240263 A1 9/2009 Kawai et al.
2009/0326559 A1 12/2009 Almodovar
2010/0042116 A1 2/2010 Chui et al.
2010/0191259 A1 7/2010 Suzuki et al.
2011/0054499 A1 3/2011 Almodovar
2011/0152891 A1 6/2011 Mclawhorn et al.
2011/0270281 A1 11/2011 Malkowski
2012/0150199 A1 6/2012 Woodard, Jr. et al.
2012/0239011 A1 9/2012 Hyodo et al.
2014/0222036 A1 8/2014 Hamilton et al.
2014/0277405 A1 9/2014 Wilson et al.
2014/0296417 A1 10/2014 Hans et al.
2015/0081014 A1 3/2015 Gross et al.
2015/0127025 A1 5/2015 Hamilton et al.
2018/0116653 A1 5/2018 Almodovar
2019/0388087 A1* 12/2019 Almodovar ........ A61B 17/0469
2021/0100549 A1 4/2021 Almodovar
2021/0298749 A1 9/2021 Smith

FOREIGN PATENT DOCUMENTS

WO WO2011029105 3/2011
WO WO2012057807 5/2012
WO WO2015074066 5/2015
WO WO2016011594 1/2016
WO WO2017091680 6/2017
WO WO2019246437 12/2019

OTHER PUBLICATIONS

International Search Report and Written Opinion dated Mar. 10, 2011 in related International Application No. PCT/US2010/054651 filed Oct. 29, 2020 (7 pages).
International Search Report and Written Opinion dated Mar. 6, 2012 in related International Application No. PCT/US2010/055370 filed Nov. 4, 2010 (10 pages).
International Search Report and Written Opinion dated Feb. 21, 2017 in related International Application No. PCT/US2016/063513 filed Nov. 23, 2016 (9 pages).
International Search Report and Written Opinion dated May 14, 2019 in related International Application No. PCT/US2019/012199 filed Jan. 3, 2019 (14 pages).
International Search Report and Written Opinion dated Jan. 10, 2019 in related International Application No. PCT/US2019/038308 filed Jun. 20, 2019 (5 pages).
International Search Report and Written Opinion dated Dec. 27, 2023 in related application PCT/US2024/044539 filed Aug. 29, 2024 (11 pages).
Japan Office Action dated Mar. 8, 2023 in related serial No. 2021-520280 filed Jun. 20, 2019 (23 pages).

* cited by examiner 28
91
89
88
79
71
69
76
78
25
102
83
68
84
78
85
23
26
90
62U
62U
62U
62U
117
d1
92
d2
86
64U
64U
62U
64U
87
110

113
110
99-2
114
26, 40
64U
64L
144-2
144-1
104
62U
93
64U
99-1
64L
102
78
98
62L
85
86
84
92
71
66
87
90
70
68 driving position
80
79
23
83
27
20

113
19
26,
40
104
102
90
110
70
114
146
87
85

20
120
140
92
720

GRIP FOR A NEEDLE DRIVER AND METHODS OF MANUFACTURE AND USE THEREOF

RELATED APPLICATIONS

This application claims the benefit of U.S. Provisional Application No. 63/535,261 filed 29 Aug. 2023; which is incorporated herein by reference in its entirety for all purposes.

TECHNICAL FIELD

Generally, this disclosure relates to surgical instruments. More particularly, this disclosure relates to needle drivers including an improved grip thereof.

BACKGROUND

A surgeon operating on a tissue within a patient may need to suture through the tissue, grasp the tissue, or dissect the tissue. However, each of these actions typically requires a set of different surgical instruments, which can be expensive to obtain, incompatible with each other, laborious to disinfect, non-ergonomic, bulky, or time consuming to insert into the patient or to withdraw from within the patient. Additionally, if suturing requires a needle and the needle varies in size, then the set of different surgical instruments may need to include a needle-specific driver, otherwise known as a needle driver.

SUMMARY OF THE INVENTION

Needle drivers can provide many benefits to surgeons or any medical professional during surgical or other medical procedures, such as during laparoscopic surgery. An exemplary needle driver is described in U.S. patent application Ser. No. 16/447,543 filed on Jun. 20, 2019, now U.S. Pat. No. 11,937,806 issued on Mar. 26, 2023 (hereinafter known as the '806 needle driver), the disclosure of which is incorporated by reference herein in its entirety.

This disclosure provides improvements upon the '806 needle driver. Specifically, the present disclosure provides an improved grip as compared to the existing grip of the '806 needle driver.

In general, according to one aspect, the present disclosure features a grip for a needle driver. The grip has a distal end located at a distal end of the needle driver and the grip includes a first jaw and a second jaw, a guard, a grasping portion and a non-grasping portion. The first jaw hosts a first roller and the second jaw hosts a second roller, and the first roller includes a first groove pattern and the second roller includes a second groove pattern. The first jaw is also pivotally connected to the second jaw via a pin located at a proximal end of the grip, where the proximal end of the grip opposes its distal end.

The guard is distributed across the first jaw and the second jaw. The guard has a back edge that faces towards the proximal end of the grip and a front edge that faces towards the distal end of the needle driver. The grasping portion extends from the front edge of the guard to the distal end of the grip, and the groove patterns of the rollers are located within the grasping portion. The non-grasping portion extends from the back edge of the guard to the pin.

Preferably, the guard prevents a needle and/or suture from entering the non-grasping portion from the front edge of the guard. For this purpose, the guard includes include a first flange that extends upward from a first side of the first jaw, a second flange that extends upward from a second side of the first jaw, and a first recess formed in a first side of the second jaw and a second recess formed in a second side of the second jaw. In more detail, the first side of the first jaw is opposite to the second side of the first jaw in a longitudinal plane that extends from the proximal end of the grip to its distal end, and the flanges each extend upward from a top surface of the first jaw to define the front edge of the guard, and then extend back downward to the top surface to define the back edge of the guard. The first side of the second jaw is opposite to the second side of the second jaw in the longitudinal plane. The first recess of the second jaw is configured to receive the first flange of the first jaw and the second recess of the second jaw is configured to receive the second flange of the first jaw, such that the first and second flanges seat within the first and second recesses, respectively, when the grip is either in a closed position or a grasping position.

Typically, each of the first and second flanges have a curved shape. In one implementation, the grip is configured to drive a needle in the grasping portion, between the first groove pattern of the first roller and the second groove pattern of the second roller when the grip is in a driving position. The driving position is defined by peaks of the first groove pattern of the first roller being in alignment with peaks of the second groove pattern of the second roller, and valleys of the first groove pattern of the first roller being in alignment with valleys of the second groove pattern of the second roller.

The grip may also include a shifting feature distributed across the first jaw and the second jaw that is configured to place the grip in a grasping position. The grasping position enables a suture to be grasped between the rollers in the grasping portion. In one example, the shifting feature is configured to move the second roller in a longitudinal plane towards the distal end of the grip and away from the first roller while the first roller remains stationary in the longitudinal plane, until the second groove pattern of the second roller overlaps the first groove pattern of the first roller to place the grip in the grasping position.

Preferably, the shifting feature includes a canted stationary member seated within the first jaw, and a beveled disc located at a back end of the second roller of the second jaw, where the back end of the second roller faces the proximal end of the grip. For this purpose, the canted stationary member can extend upward from a top surface of the first jaw, is canted towards the proximal end of the grip, and is canted in the proximal direction away from a vertical plane that is perpendicular to the top surface of the first jaw. In one implementation, the beveled disc has a diameter larger than a diameter of a second groove pattern of the second roller.

In another implementation of the grip, each of the first and second groove patterns includes a plurality of peaks and valleys, and prior to the grip being in its grasping position, the shifting feature begins to be deployed when a beveled edge of the beveled disc comes into contact with a front face of the canted stationary member to define a shifting feature roller gap distance between opposing valleys of the first and second groove patterns. When a suture having a diameter that is smaller than the shifting feature roller gap distance is located between the opposing valleys, the beveled edge of the beveled disc can be increasingly configured to impinge upon the front surface of the canted stationary member until the second groove pattern of the second roller overlaps the first groove pattern of the first roller to grasp the suture between the rollers.

In general, according to another aspect, the present disclosure features a grip for a needle driver. The needle driver includes a grip located at a distal end of the needle driver. The grip includes a first jaw and a second jaw, a guard distributed across the first jaw and the second jaw, a grasping portion that extends from the front edge of the guard to the distal end of the grip, a non-grasping portion and an actuating mechanism.

The first jaw hosts a first roller and the second jaw hosts a second roller. The first roller includes a first groove pattern and the second roller includes a second groove pattern. Additionally, the first jaw is pivotally connected to the second jaw via a pin located at a proximal end of the grip, where the proximal end of the grip opposes its distal end. The guard has a back edge that faces towards the proximal end of the grip and a front edge that faces towards the distal end of the needle driver. The groove patterns of the rollers are located within the grasping portion, and the non-grasping portion extends from the back edge of the guard to the pin.

The actuating mechanism is connected to the grip and is configured to enable the grip to drive a needle into tissue of a patient when the needle is located in the grasping portion. The actuating mechanism is also configured to enable the grip to grasp a needle and/or suture when the needle and/or suture is located in the grasping portion.

The guard prevents a needle and/or suture from entering the non-grasping portion from the front edge of the guard.

The needle driver also includes a shifting feature distributed across the first jaw and the second jaw. The shifting feature is configured to place the grip in a grasping position that enables a suture to be grasped between the rollers in the grasping portion. In one example, the shifting feature moves the second roller in a longitudinal plane towards the distal end of the grip and away from the first roller while the first roller remains stationary in the longitudinal plane, until the second groove pattern of the second roller overlaps the first groove pattern of the first roller to place the grip in the grasping position. For this purpose, the shifting feature includes a canted stationary member seated within the first jaw, and a beveled disc located at a back end of the second roller of the second jaw, where the back end of the second roller faces the proximal end of the grip.

Preferably, the canted stationary member extends upward from a top surface of the first jaw, is canted towards the proximal end of the grip, and is canted in the proximal direction away from a vertical plane that is perpendicular to the top surface of the first jaw.

In another implementation, each of the first and second groove patterns includes a plurality of peaks and valleys. Prior to the grip being in its grasping position, the shifting feature begins to be deployed when a beveled edge of the beveled disc comes into contact with a front face of the canted stationary member to define a shifting feature roller gap distance between opposing valleys of the first and second groove patterns. When a suture having a diameter that is smaller than the shifting feature roller gap distance is located between the opposing valleys, the beveled edge of the beveled disc can be increasingly configured to impinge upon the front surface of the canted stationary member until the second groove pattern of the second roller overlaps the first groove pattern of the first roller to grasp the suture between the rollers.

In one embodiment, the needle driver is a robotic needle driver that includes a robotic system, and the robotic system is the actuating mechanism. In another embodiment of the needle driver, the actuating mechanism is a handle accommodated within a housing and includes at least one rotating shaft under control of the handle, and the at least one rotating shaft connects to the grip.

In general, according to yet another aspect, the present disclosure features a method for a needle driver including a grip, the grip having a distal end located at a distal end of the needle driver, and the grip comprising a first jaw and a second jaw. The first jaw hosts a first roller and the second jaw hosts a second roller, and the first roller includes a first groove pattern and the second roller includes a second groove pattern. The first jaw is pivotally connected to the second jaw at a proximal end of the grip, the proximal end of the grip opposing its distal end.

The method comprises the steps of: enabling a needle to be driven between the groove patterns of the rollers within a grasping portion of the grip; enabling a suture to be grasped between the rollers within the grasping portion of the grip; and preventing the needle and/or suture from entering a non-grasping portion of the grip located near its proximal end, the non-grasping portion pivotally connecting the first jaw to the second jaw via a pin located at the proximal end.

In one implementation, the step of enabling a needle to be driven between the groove patterns of the rollers within a grasping portion of the grip comprises: locating the needle between the groove patterns of the rollers; and configuring the grip to be in a driving position defined by peaks of the first groove pattern of the first roller being in alignment with peaks of the second groove pattern of the second roller, and defined by valleys of the first groove pattern of the first roller being in alignment with valleys of the second groove pattern of the second roller.

In another implementation, the step of enabling a suture to be grasped between the rollers within the grasping portion of the grip comprises locating the needle between the groove patterns of the rollers, and configuring the grip to be in a grasping position, the grasping position enabling the needle and/or suture to be grasped between the rollers.

In one example, configuring the grip to be in a grasping position comprises moving the second roller in a longitudinal plane towards the distal end of the grip and away from the first roller while the first roller remains stationary in the longitudinal plane, until the second groove pattern of the second roller overlaps the first groove pattern of the first roller.

In another implementation, the step of enabling a suture to be grasped between the rollers within the grasping portion of the grip comprises: each of the first and second groove patterns including a plurality of peaks and valleys; distributing a shifting feature across the first jaw and the second jaw, the shifting feature including a canted stationary member located in the first jaw, and a beveled disc located at a back end of the second roller of the second jaw, the back end of the second roller facing the proximal end of the grip; starting deployment of the shifting feature, where the starting causes a beveled edge of the beveled disc to come into contact with a front face of the canted stationary member to define a shifting feature roller gap distance between opposing valleys of the first and second groove patterns; locating a suture having a diameter that is smaller than the shifting feature roller gap distance between the opposing valleys; and increasingly impinging the beveled disc upon the front surface of the canted stationary member until the second groove pattern of the second roller overlaps the first groove pattern of the first roller to grasp the suture between the rollers.

In still another implementation, the step of preventing a needle and/or suture from entering a non-grasping portion of the grip located near its proximal end comprises distributing a needle guard across the first jaw and the second jaw, the guard having a back edge that faces towards the proximal end of the grip and a front edge that faces towards the distal end of the needle driver, the non-grasping portion extending from the back edge of the guard to the pin, and the front edge of the needle guard preventing the needle and/or suture from entering the non-grasping portion of the grip.

Preferably, the grasping portion extends from the front edge of the guard to the distal end of the grip.

The method can further comprise the step of actuating the grip to drive the needle and/or to grasp the suture via a robotic system connected to the grip. The method can further comprise the step of actuating the grip to drive the needle and/or to grasp the suture, via a handle accommodated within a housing, the handle including at least one rotating shaft connected to the grip and the rotating shaft being under control of the handle.

The above and other features of the present disclosure including various novel details of construction and combinations of parts, and other advantages, will now be more particularly described with reference to the accompanying drawings and pointed out in the claims. It will be understood that the particular method and device embodying the present disclosure are shown by way of illustration and not as a limitation of the inventions covered by the present disclosure. The principles and features of the present disclosure may be employed in various and numerous embodiments, including any combination of embodiments described herein, without departing from the scope of the inventions covered by the present disclosure.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the present disclosure. Of the drawings.

DETAILED DESCRIPTION OF THE PREFERRED EMBODIMENTS

Figure 1:
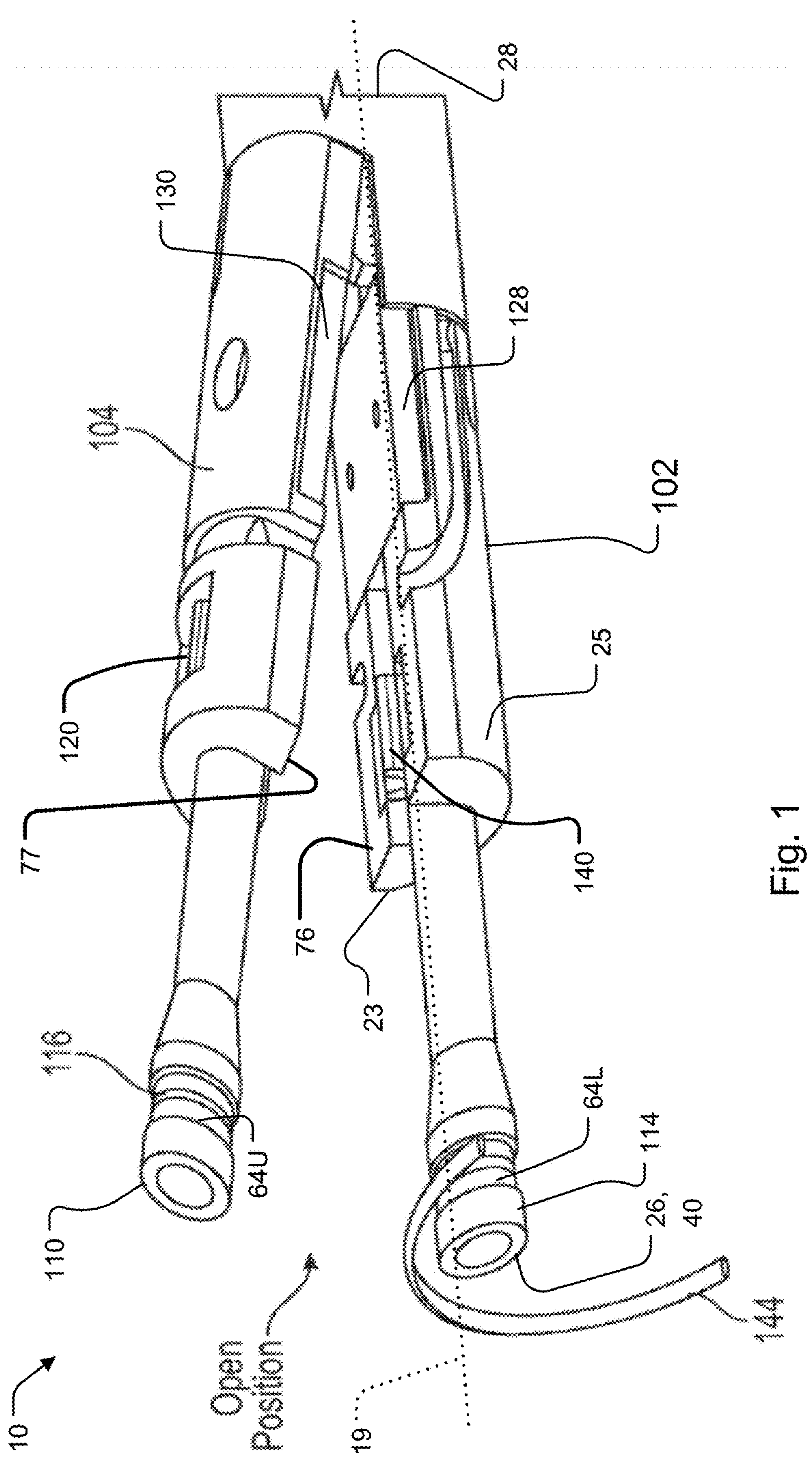
FIG. 1 is a perspective view of an existing grip of the prior art '806 needle driver, where the view illustrates aspects of the existing grip that the proposed inventive grip improves upon.

The present disclosure now will be described more fully hereinafter with reference to the accompanying drawings, in which illustrative embodiments of the disclosure are shown. The inventions covered by this disclosure may, however, be embodied in many different forms and should not be construed as limited to the embodiments set forth herein; rather, these embodiments are provided so that this disclosure will be thorough and complete, and will fully convey the scope of the inventions to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

As used herein, a term "or others," "combination", "combinatory," or "combinations thereof" refers to all permutations and combinations of listed items preceding that term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. Skilled artisans understand that typically there is no limit on number of items or terms in any combination, unless otherwise apparent from the context.

Further, it will be understood that when an element, including component or subsystem, is referred to and/or shown as being "connected" or "coupled" to another element, it can be directly connected or coupled to the other element or intervening elements may be present. In contrast, when an element is referred to as being "directly connected" or "directly coupled" to another element, then there are no intervening elements present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 shows an exemplary existing grip 10 of the prior art '806 needle driver. The '806 needle driver typically includes a handle (not shown), and a substantially longitudinal and cylindrical member, also known as a tube (not shown), that connects the handle to the grip 10. The grip 10 has articulating jaws which include an upper jaw 104 and a lower jaw 102. The grip 10 is located at a distal end 40 of the needle driver, while the handle is located at a proximal end of the needle driver that opposes its distal end 40.

The grip 10 has a distal end 26 that coincides with the distal end 40 of the needle driver and has a proximal end 28 that opposes its distal end 26. The proximal end 28 of the grip 10 connects to the tube (not shown).

Each of the jaws 104, 102 hosts or otherwise includes a roller. The upper jaw 104 includes an upper roller 110 and the lower jaw 102 includes a lower roller 114. The rollers 110, 114 extend longitudinally from the distal end 26 of the grip 10 towards its proximal end 28 and have identical profiles with respective groove patterns. Each of the groove patterns has a plurality of grooves. The grooves define a plurality of peak/valley portions, male/female portions, or projection/depression portions, any of which can be perpendicular to the roller or non-perpendicular to the roller (e.g., acute, obtuse). For example, the grooves can be slanted, wavy, pulse-shaped, or others. For example, the grooves can be internally U-shaped, C-shaped, V-shaped, W-shaped, or others.

In the illustrated example, the jaws 104, 102 are in an open position, and thus the existing grip 10 is shown in its open position. A needle 144 is shown resting within a lower valley 64L of the lower roller 114 at the distal end 26 of the grip 10.

The existing grip 10 has a right side 25 that faces the viewer and a left side 23 that opposes its right side 25. The lower jaw 102 has a substantially flat top surface 76 and includes a set of lower teeth 140 that seat within a recess formed in the lower jaw 102. The upper jaw 104 has a substantially flat underside surface 77 (not visible) and includes a set of upper teeth 120 that seat within a recess of the upper jaw 104. The lower teeth 140 partially protrude above the top surface 76 and the upper teeth partially protrude below the underside surface 77, and the teeth 140, 120 are configured to oppose one another.

The existing grip 10 also includes a lower retaining block 128 hosted within the lower jaw 102 and an upper retaining block 130 hosted within the upper jaw 104. The retaining blocks 128, 130 have substantially flat surfaces and face each other. In the illustrated example, the lower retaining block 128 is coplanar with the top surface 76 and the upper retaining block 130 is coplanar with the underside surface 77.

When the jaws 104, 102 are closed, the rollers 110, 114 oppose one another in a substantially longitudinal plane 19, and the grooves of the rollers (e.g., the peak/valley portions, and the like) are aligned and parallel to each other. The needle 144 seats within a lower valley 64L of the lower roller 114 and an opposing upper valley 64U of the upper roller 110. The teeth 140, 120 engage with each other, the top surface 76 and the underside surface 77 are in mating contact with each other, and the retaining blocks 128, 130 are also in mating contact with each other.

The existing grip 10 has multiple uses. In one example, the grip 10 can grasp and hold a needle and/or a suture between the upper jaw 104 and the lower jaw 102. For this purpose, a surgeon opens the jaws 104, 102 via the handle, and places the needle and/suture either between the surfaces of the retaining blocks 128, 130. The surgeon then closes the jaws 104, 102 via the handle, thus grasping the needle and/or suture between the surfaces. In another example, the grip 10 can "drive" a needle, with a suture attached to the needle, into tissue of a patient to accomplish suturing of the patient. Here, the surgeon opens the jaws 104, 102, places the needle between the valley portions 64U, 64L of the opposing rollers 110, 114 such that the length of the needle is substantially transverse to the longitudinal plane 19, and closes the jaws to "capture" the needle between the rollers 110, 114. The surgeon can then use the handle to rotate the rollers, the result of which drives the needle and suture in a direction that is transverse to the longitudinal plane 19. The act of driving a needle (or other sharp object) can also be used to puncture, dissect or otherwise create openings in tissue, in other examples.

One of the primary uses of the needle driver is laparascopic surgery. For this purpose, the existing grip 10 is placed within a body cavity of a patient, where the body cavity includes the tissue that is the target of the surgical procedure. Typically, an incision is made in the body of the patient, and via the incision (or a different incision), the surgeon places a camera in the target surgical area via a surgical device that is separate from the needle driver. The surgeon then uses the same incision (or possibly a different incision) to guide the existing grip 10 of the needle driver into the body cavity.

The camera, in turn, has a light that illuminates the target tissue and connects to a video monitor. The camera presents frames of two-dimensional (2D) image data of the illuminated target area to the video monitor. The surgeon then views the frames of 2D image data on the video monitor to guide and operate the existing grip 10 to grasp needles and/or sutures, and to drive needles into the target tissue.

During a surgical procedure, the surgeon typically orients the camera in at least two directions. In a first direction, the surgeon places the camera behind the existing grip 10, such that the camera lens points towards the distal end 40 of the needle driver and along a line of sight that coincides with the longitudinal plane 19. In a second direction, the surgeon places the camera lens to face either of the sides 23, 25 of the existing grip 10, such that the line of sight of the camera lens is substantially perpendicular/transverse to the longitudinal plane 19. Other orientations of the camera that provide angled views of the existing grip 10, the needles and sutures, and the target tissue are also possible.

Experimentation has shown that surgeons can use the existing grip 10 to repeatably and consistently drive needles into tissue. While the same surgeons are also able to grasp needles and/or sutures with the existing grip 10, the surgeons have not been able to grasp the needles and/or sutures as consistently as in the case of driving the needles.

A number of factors contribute to the inconsistency that surgeons sometimes experience when grasping needles and sutures with the existing grip 10. In one example, the view of the target scene provided by the 2D image data lacks depth because of its 2D nature. In another example, the view might not allow the surgeon to move the grip 10 such that a needle or suture enters the open jaws 102, 104 of the grip 10 from its sides 23, 25. This is especially the case when the camera is located behind the grip 10, because the sides 25, 23 of the jaws and the pair of opposing surfaces 128, 130 might be only partially visible in the view, or not visible at all.

In yet another example, the surgeon might not be able to consistently place the needle in the valley portions 64U and 64L of the existing grip 10 and might not be able to consistently place the suture between the surfaces 128 and 130 of the grip 10. If the needle is not placed in the valley portions 64U, 64L, the surgeon will not be able to drive the needle. In a similar vein, the surgeon will not be able to grasp the suture if the suture is not placed between the surfaces 128 and 130. To address these issues, the surgeon has to release, reposition, and regrasp the needle or suture.

Figure 2:
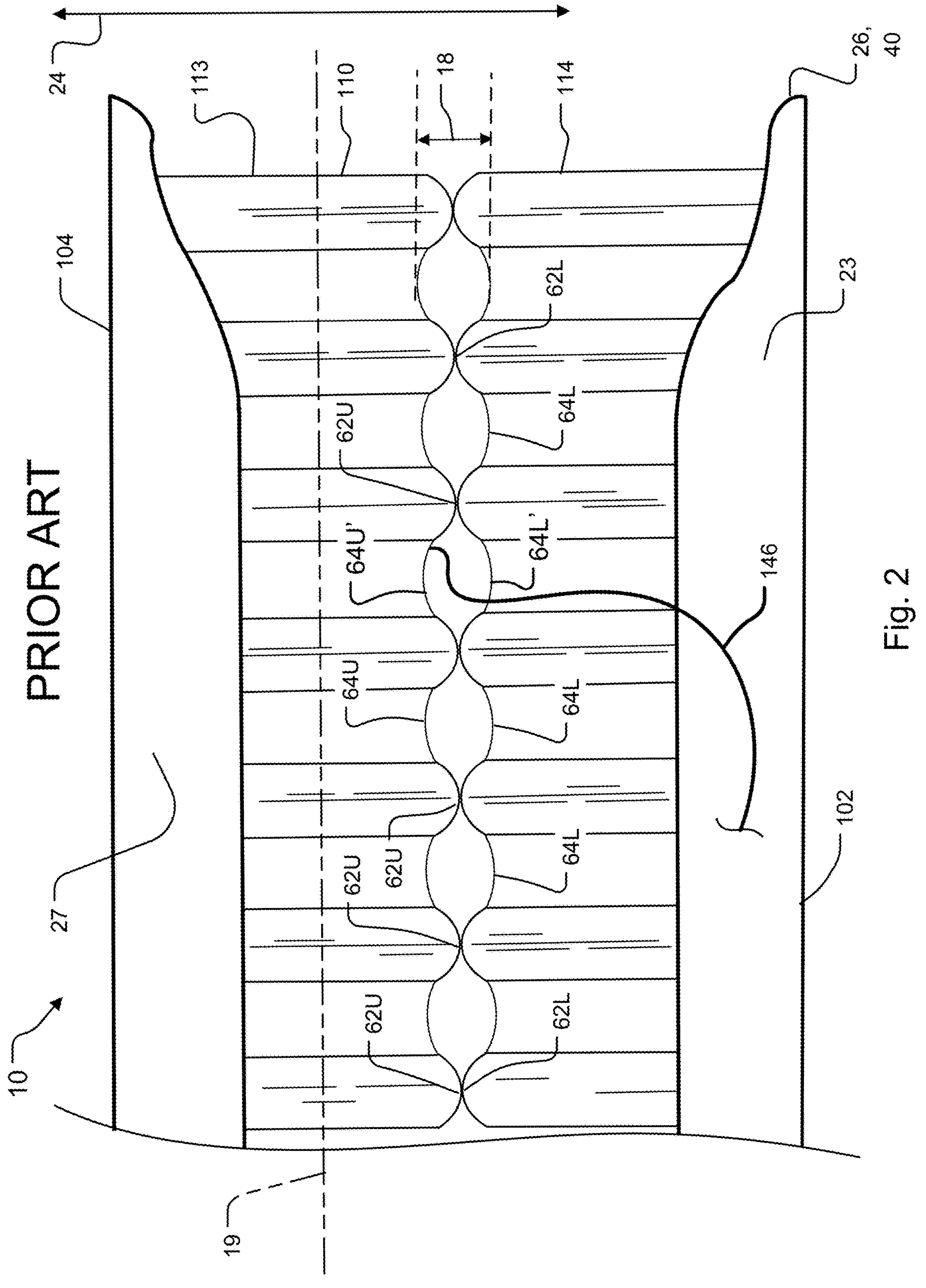
FIG. 2 is a magnified side view of a portion of the existing grip of FIG. 1, viewed at a distal end of the '806 needle driver, where the figure shows the grip in a closed position, and where the figure shows that the existing grip is unable to grasp a suture between its rollers.

FIG. 2 is an enlarged side view of a portion of the existing grip 10, at the distal end 40 of the needle driver 600/at the distal end 26 of the grip 10. This figure illustrates how a small object such as a suture 146 can be positioned within a pair of opposing valleys 64L, 64U of the rollers 110, 114, and the existing grip 10 is unable to grasp the suture 146 between the rollers 110, 114 when the grip 10 is in its closed position.

A minimum roller gap distance 18 of the existing grip 10 is defined as the distance between any opposing valleys 64L, 64U of the rollers 114, 110 when the grip 10 is in its closed position. In the illustrated example, the existing grip 10 is in its closed position and the suture 146 is positioned between opposing valleys 64L' and 64U'. Because the thickness/diameter of the suture 146 is less than the minimum roller gap distance 18, the grip 10 cannot grasp the suture 146 between the rollers 110, 114.

An inventive grip is proposed that provides various improvements to the existing grip 10 of the '806 needle driver. The inventive grip of the present application overcomes the limitations of the existing grip 10 with regards to grasping of needles and/or sutures, while also providing the ability to repeatably and consistently drive needles. Moreover, the inventive grip requires less movement of the needle driver and grip by the surgeon during a procedure to grasp a needle or suture. This reduces surgeon fatigue, which correspondingly reduces procedure time and improves patient outcomes.

In one embodiment, the inventive grip is configured to include a guard that is distributed across the jaws 102, 104. The guard prevents a needle 144 and/or suture from entering a non-grasping portion of the grip. In another embodiment, the proposed grip is configured to include a shifting feature that is distributed across at least one of the jaws and at least one of the rollers. The shifting feature is deployed in order to grasp a suture between the rollers in a grasping portion of the grip. When deployed, the shifting feature "shifts" or moves one of the rollers in a longitudinal direction towards the distal end of the needle driver, while the other roller remains stationary in the longitudinal direction, until the peaks of one roller are seated within the valleys of the other roller. Deployment of the shifting feature allows the suture to be reliably and consistently grasped and held between the rollers in the grasping position of the grip. More detail regarding the inventive grip is included in the descriptions of FIG. 3 through FIG. 10, included herein below.

Figure 3:
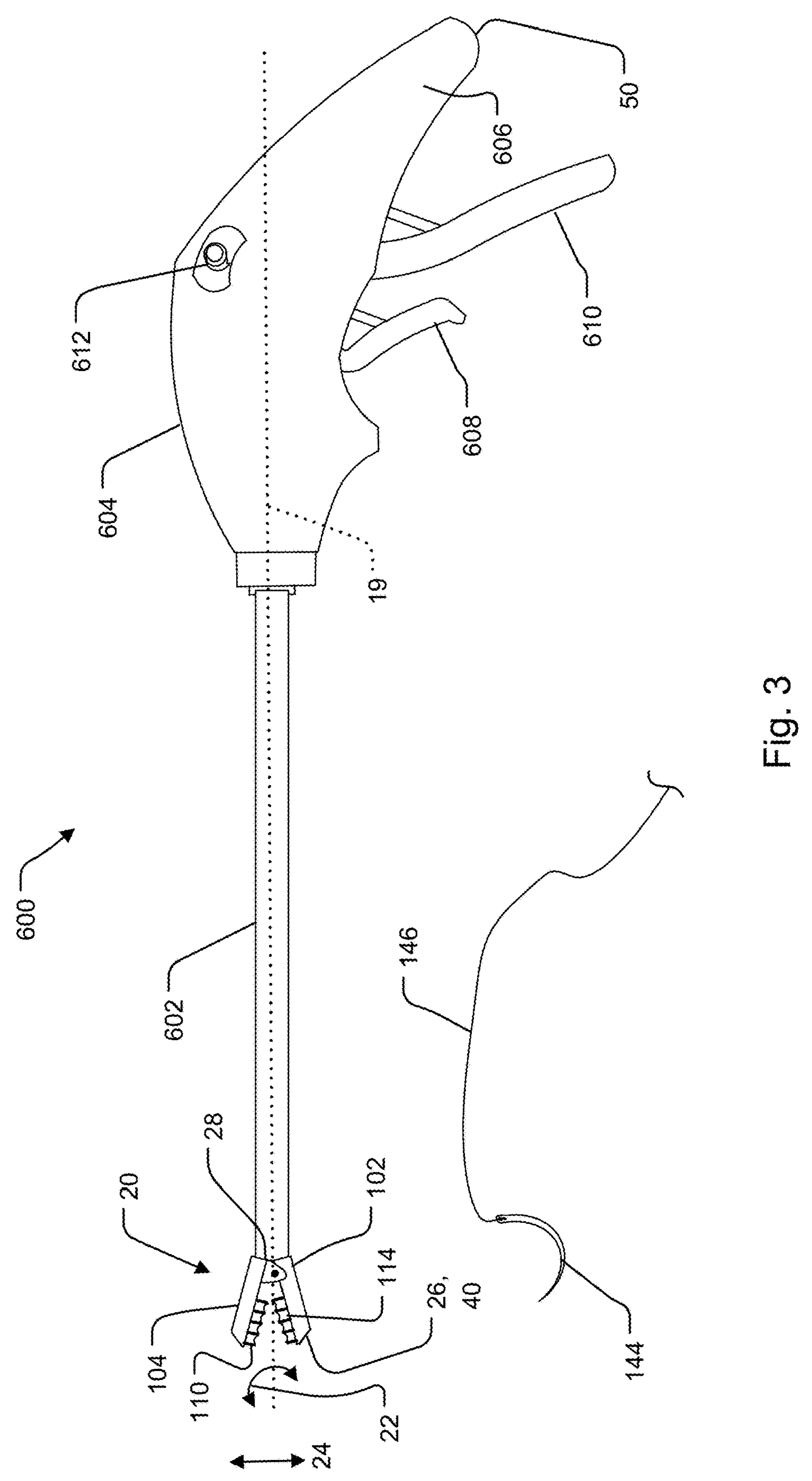
FIG. 3 is a schematic diagram of an exemplary needle driver that includes the inventive grip, according to an embodiment, where the needle driver includes a handle with at least one rotating shaft connected to the grip as an actuating mechanism for manipulating the grip.

FIG. 3 shows an exemplary needle driver 600 that includes a grip 20 constructed in accordance with principles of the present disclosure. The needle driver 600 additionally includes a handle 604 and a tube 602 that connects the grip 20 to the handle 604. An exemplary needle 144 and a suture 146 attached to the needle 144 are also shown.

The grip 20 is located at the distal end 40 of the needle driver 600 and includes an upper jaw 104 and a lower jaw 102. The upper jaw 104 includes or otherwise hosts an upper roller 110 and the lower jaw 102 includes or otherwise hosts a lower roller 114. The grip 20 has a distal end 26 that faces the distal end 40 of the needle driver 600 and has a proximal end 28 that opposes its distal end 26. One end of the tube 602 attaches to the grip 20 at the proximal end 28 of the grip 20, while an opposing end of the tube 602 attaches to the handle 604.

The handle 604 is housed by or otherwise accommodated within a housing 606. The handle includes a lever 610, a trigger 608 and a switch 612. The handle 604 is located at a proximal end 50 of the needle driver 600 that opposes the distal end 40.

The needle driver 600 generally operates as follows. The lever 610 and the trigger 608 are pressed towards the proximal end 50 and/or released away from the proximal end 50. These pressing and releasing actions of the lever 610 and the trigger 608 cause gears (not shown) within the handle 604 to rotate, and the gear rotation is translated to rotational motion of shafts (not shown) located within the tube 602. The shafts typically extend to the grip 20, where at least one of the shafts connects to the grip 20.

In more detail, a surgeon or other medical professional can press and release the lever 610 to respectively open and close the jaws 104, 102. This opening and closing motion is indicated by reference 24. In the illustrated example, the lever 610 is in its open position. Correspondingly, the grip 20 is in its open position/the jaws 102, 104 are open.

When the surgeon intends to drive a needle 144 via the rollers 110, 114 or grasp a suture 146 between the rollers, the surgeon first moves the needle driver 600 and grip 20 until the needle 144 or suture 114 is located between the rollers 110, 114. In the case of the needle 144, the surgeon arranges the grip 20 such that the needle 146 is located between a pair of opposing valleys 64U, 64L of the rollers 110, 114 and is transverse to the longitudinal plane 19. The surgeon then presses the lever 610 towards the housing 606, and the jaws 104, 102 begin to close. The surgeon continues pressing the lever 610 until the lever locks in place near the housing 606. In one implementation, the lever 610 provides a ratcheting style locking and unlocking mechanism.

When the lever 610 is locked with a needle 144 between the rollers 110, 114, a friction force is applied to the rollers. This force holds the needle 114 between the rollers while also enabling the rollers to rotate. This places the grip 20 in a driving position. The trigger 608, when pressed and released, causes both of the rollers 110, 114 to rotate and drives the needle 114 between the rollers 110, 114. Experience has shown that a typical needle 144 moves approximately 25 percent of its length in a direction that is transverse to the longitudinal plane 19, in response to each press and release of the trigger 608.

When the lever 610 is locked with a suture 146 between the rollers 110, 114, a friction force is applied to the rollers that engages the shifting feature. This places the grip 20 in a grasping position. In response, the rollers 110, 114 overlap to grasp the suture 146. Here, the force applied to the rollers 110, 114 is typically greater than that applied during the driving of needles described herein above. As a result, the trigger 608 is typically inoperative when the lever 610 is locked and the grip 20 is in its grasping position.

To unlock the lever 610, the surgeon further presses the lever 610 towards the housing 606 until the lever 610 unlocks. In this way, based on surgical objectives, the surgeon can repeatedly place the grip 20 in its open position followed by its driving position to drive a needle, place the grip back in its open position to readjust the grip 20 relative to the needle, and place the grip 20 back in its driving position to again drive the needle 144. In a similar vein, the surgeon can repeatedly place the grip 20 in its open position followed by its grasping position to grasp a suture 146, place the grip back in its open position to readjust the grip 20 relative to the suture, and place the grip 20 back in its grasping position to again grasp the suture 146. Additionally and/or alternatively, the surgeon can manipulate the grip 20 to alternate between driving needles 144 and grasping sutures 146.

The switch 612 has two positions which control whether the rollers 110, 114 rotate in a clockwise or a counterclockwise direction with each press and release of the trigger 608. This direction of rotational motion of the rollers 110, 114 is indicated in the figure by reference 22. For example, when the switch 612 is in the first position (e.g., toward the distal end 40 of the needle driver 600), pressing and releasing the trigger 608 causes the rollers 110 and 114 to rotate such that the needle 114 is moved in a leftward or counterclockwise direction when viewing the needle driver 600 from its proximal end 50 to its distal end 40. When the switch 612 is moved to its second position (e.g., toward the proximal end 50 of the needle driver 600), pressing and releasing the trigger 608 causes the rollers 110 and 114 to rotate such that the needle is moved in a rightward or clockwise direction when viewing the needle driver 600 from its proximal end 50 to its distal end 40.

In an embodiment, the needle driver 600 is designed to drive at least two of the most common needles, namely, SH-1 and RB-1 needles, but this application is not limited thereto, and the needle driver described herein can be used with any needle suitable for surgical use including non-SH and non-RB type needles. The SH-1 and RB-1 needles have a typical diameter of 0.58 millimeters (mm) and 0.42 mm, respectively. The diameter of a typical suture can be about 0.14 mm to about 0.20 mm, or possibly as large as 0.40 mm. For example, the diameter of a suture can be about 0.10 mm, about 0.11 mm, about 0.12 mm, about 0.13 mm, about 0.14 mm, about 0.15 mm, about 0.16 mm, about 0.17 mm, about 0.18 mm, about 0.19 mm, about 0.20 mm, about 0.25 mm, about 0.30 mm, about 0.35 mm, about 0.40 mm, or any diameter in between the foregoing diameters. As a result, the needle driver 600 is typically able to drive needles of 0.42 mm in diameter and greater. It can also be appreciated that at least one rotating shaft of the handle 604 connects to the grip 20. For this reason, the handle 604 and its at least one rotating shaft form an actuating mechanism of the needle driver 600 for manipulating the grip 20. The handle 604 and its at least one rotating shaft operates as an actuating mechanism for manipulating the grip 20 to be in its open, driving and grasping positions.

Figure 4:
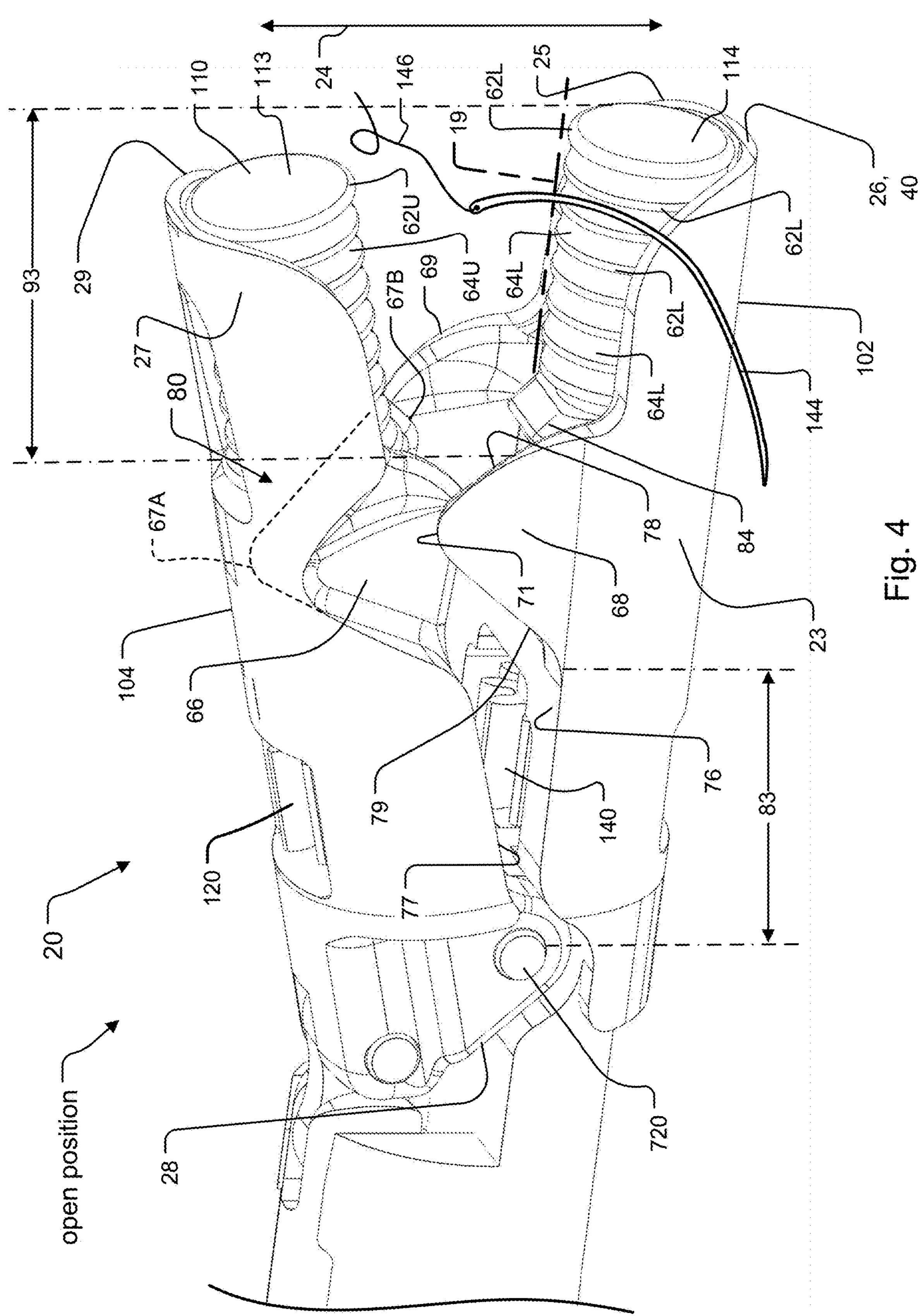
FIG. 4 is a perspective side view of the inventive grip, according to an embodiment, that shows the grip in an open position, where a proposed guard feature is distributed across the upper and lower jaws.

FIG. 4 is an enlarged view of the upper jaw 104 and the lower jaw 102 of the grip 20 when the grip is in its open position, according to an embodiment. This view shows additional components of and more detail for the grip 20.

The grip 20 additionally includes a pin 720 and a guard 80. A non-grasping portion 83 and a grasping portion 93 of the grip 20 are also shown. The grasping portion 93 extends from the distal end of the grip 26 to a front edge of the guard 80, while the non-grasping portion 83 extends from a back edge of the guard to the pin 720 near the proximal end 28 of the grip 20.

The upper roller 110 has a front end 113 that faces the distal end 26 of the grip 20. The upper roller 110 includes peaks 62U and valleys 64U, while the lower roller 114 includes peaks 62L and valleys 64L. An exemplary needle 144 with an attached suture 146 is loosely placed within a valley 64L of the lower roller 114.

The upper jaw 104 is pivotally coupled to the lower jaw 102 via the pin 720. In the non-grasping portion 83, the lower jaw 102 has a substantially flat top surface 76. A longitudinal plane 19 of the rollers 110, 114 is also shown. The lower jaw 102 has a left side 23 and a right side 25 that oppose one another. The left and right sides 23, 25 are also located on opposite sides of the lower roller 114, along its length/in the direction of the longitudinal plane 19. In a similar vein, the upper jaw 104 has a left side 27 and a right side 29 that oppose one another. The left and right sides 27, 29 are also located on opposite sides of the upper roller 110, along its length/in the direction of the longitudinal plane 19 (when the jaws are closed).

The guard 80 prevents a needle 144 and/or a suture 146 from entering the non-grasping portion 83 of the grip 20 when the jaws 102, 104 are open (partially or completely). For this purpose, the guard 80 is distributed across the upper and lower jaws 104, 102. In more detail, the guard 80 includes a left flange 68 that extends upward from the left side 23 of the lower jaw 102 and a right flange 69 that extends upward from the right side 25 of the lower jaw 102. In the illustrated example, the flanges 68, 69 have the same shape and oppose one another with respect to the longitudinal plane 19.

Additional detail for the guard 80 is as follows. The guard 80 has a front edge 78 that faces towards the distal end 26 of the grip 20 and a back edge 79 that faces towards the proximal end 28 of the grip 20. The guard 80 also includes a left recess 66 within the left side 27 of the upper jaw 104 and a right recess 67 (67A, 67B) within the right side 29 of the upper jaw 104. Most of the right recess is shown in phantom and indicated by reference 67A, while a small visible portion of the recess 67 is indicated by reference 67B. The left recess 66 has an outline that mimics the shape of the left flange 68 and is configured to receive the left flange 68. In a similar vein, the right recess 67 has an outline that mimics the shape of the right flange 69 and is configured to receive the right flange 69. When the grip 20 is in a closed position, the flanges 68, 69 are completely seated within their respective recesses 66, 67.

In one implementation, as shown, the flanges 68, 69 have a curved shape with a smooth edge designed to minimize friction when coming into contact with a needle 144 or a suture 146. Here, each of the flanges 68, 69 rise upward at the front edge 78 of the guard 80, from the top surface 76 of the lower jaw 102, towards the upper jaw 104, to a peak 71 of each flange 68, 69. Each of the flanges 68, 69 then extend downward from their peaks 71, at the back edge 79 of the guard 80, back to the top surface 76 of the lower jaw 102.

The guard 80 also defines the boundaries of the non-grasping portion 83 and the grasping portion 93. The non-grasping portion 83 extends from the back edge 79 of the guard 80 to the pin 720. The grasping portion 93 extends from the front edge 78 of the guard 80 to the distal end 26 of the grip 20. The guard 80 ensures that all driving of needles 114 and grasping of sutures occur in the grasping portion 93 of the grip 20.

Other implementations of the guard 80 are possible. In one example, a first structure resembling the flanges 68, 69 extends upward from the lower jaw 102 and is oriented substantially across the sides 23, 25 of the lower jaw 102. A second structure resembling the flanges 68, 69 extends downward from the upper jaw 104 and is oriented substantially across the sides 27, 29 of the upper jaw 104, where the first and second structures are configured to overlap. In this way, as the jaws 102,104 close, the overlapping first and second structures prevent an object such as a needle or suture from entering the non-grasping portion 83. It can also be appreciated that either the first structure can be placed in front of the second structure (i.e., the first structure is closer to the distal end 40 of the needle driver 600) to accomplish the overlapping, or vice-versa.

Figures 5A, 5B:
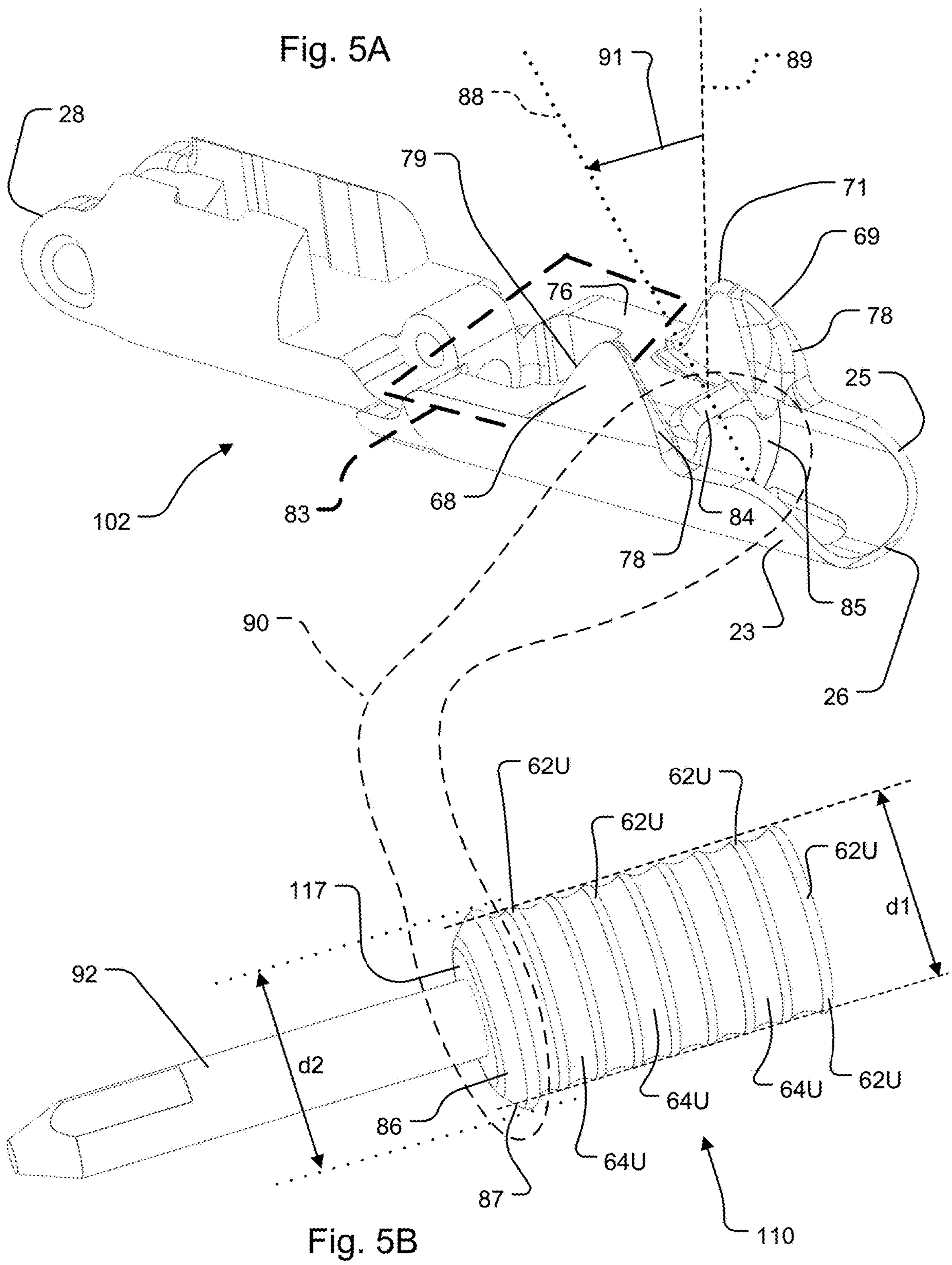
FIGS. 5A and 5B collectively show components of a shifting feature of the inventive grip, according to an embodiment, where the shifting feature enables the grip to operate in a grasping position for grasping a suture between the rollers.

FIGS. 5A and 5B collectively show components of the shifting feature, according to an embodiment. The shifting feature is indicated by reference 90 and is shown as a dotted line that encompasses portions of both FIGS. 5A and 5B.

In more detail, FIG. 5A is perspective view of the lower jaw 102 isolated from the upper jaw 104 and without its lower roller 114. This enables the display of a cantered stationary member 84 of the shifting feature 90 that is included in the lower jaw 102. FIG. 5B is a perspective view of the upper roller 110 in isolation. This enables the display of a beveled disc 86 of the upper roller 110 (a beveled disc 86 of the shifting feature 90), which is located at a back end 117 of the upper roller 110.

The shifting feature 90 is distributed across the lower and upper jaws 102, 104. In one implementation, the shifting feature 90 includes a canted stationary member 84 of the lower jaw 102, shown in FIG. 5A, and the beveled disc 86 of the upper roller 110, shown in FIG. 5B.

Returning to FIG. 5A, the canted stationary member 84 seats within the lower jaw 102 and has a front surface 85 that faces towards the distal end 26 of the grip 20. The canted stationary member 84 extends upward from the top surface 76 of the lower jaw 102 and is canted towards the proximal end 28 of the grip 20. The canted stationary member 84 is also canted in the proximal direction away from a vertical plane 89 that is perpendicular to the top surface 76 of the lower jaw 102. A canted plane 88 of the canted stationary member 84 is also shown, where the canted plane 88 is coplanar with the front surface 85 of the member 84 and is canted away from the vertical plane 89 towards the proximal end 28 of the grip 20. An amount or degree of the canting from the vertical plane 89 to the canted plane 88 is indicated by an arrow with reference 91, also known as a degree of cant 91.

The canted stationary member 84 also has a hole formed in its center. The hole allows a shaft (not shown) that connects to the lower roller 114 to pass through the hole, so that the canted stationary member 84 does not interfere with or prevent rotation of the lower roller 114 within the lower jaw 102.

More detail for the degree of cant 91 is as follows. An optimal value of the degree of cant 91 is about 45 degrees, and a working range is typically between 40 degrees and 50 degrees. Experimentation has shown that for values less than 45 degrees/as the angle decreases, the level of shifting increases but with greater friction upon the rollers 110, 114 during shifting. In a similar vein, experimentation has shown that for values of the degree of cant 91 greater than 45 degrees/as the angle of the degree of cant 91 increases, the level of shifting of the upper roller 110 relative to the lower roller 114 decreases and with less friction upon the rollers during shifting.

In FIG. 5B, the beveled disc 86 is located at a back end 117 of the upper roller 110. The beveled disc 86 has a diameter d2 and a beveled edge 87. The diameter d2 is slightly larger than the diameter d1 of the portion of the upper roller 110 that includes its peaks 62U and valleys 64U. The beveled disc 86 also connects to a shaft 92. The shaft 92 enables the upper roller 110 to rotate but it is not a component of the shifting feature 90.

In one implementation, the diameter d2 of the beveled disc 86 is about 8.5% larger than the diameter d1 of the upper roller 110. Experience has shown that as the diameter d2 of the beveled disc 86 increases beyond 10% of d1, the amount of shifting increases, but can limit the size of the needles that the grip 20 can drive. A pair of exemplary values for the diameters d1, d2 of the upper roller 110 and the beveled disc 86 are approximately 2.50 mm and 2.73 mm, respectively. In another implementation, the diameter d2 of the beveled disc 86 is larger than the diameter d1 of the upper roller 110 in a range between 7% and 13%.

Figure 6:
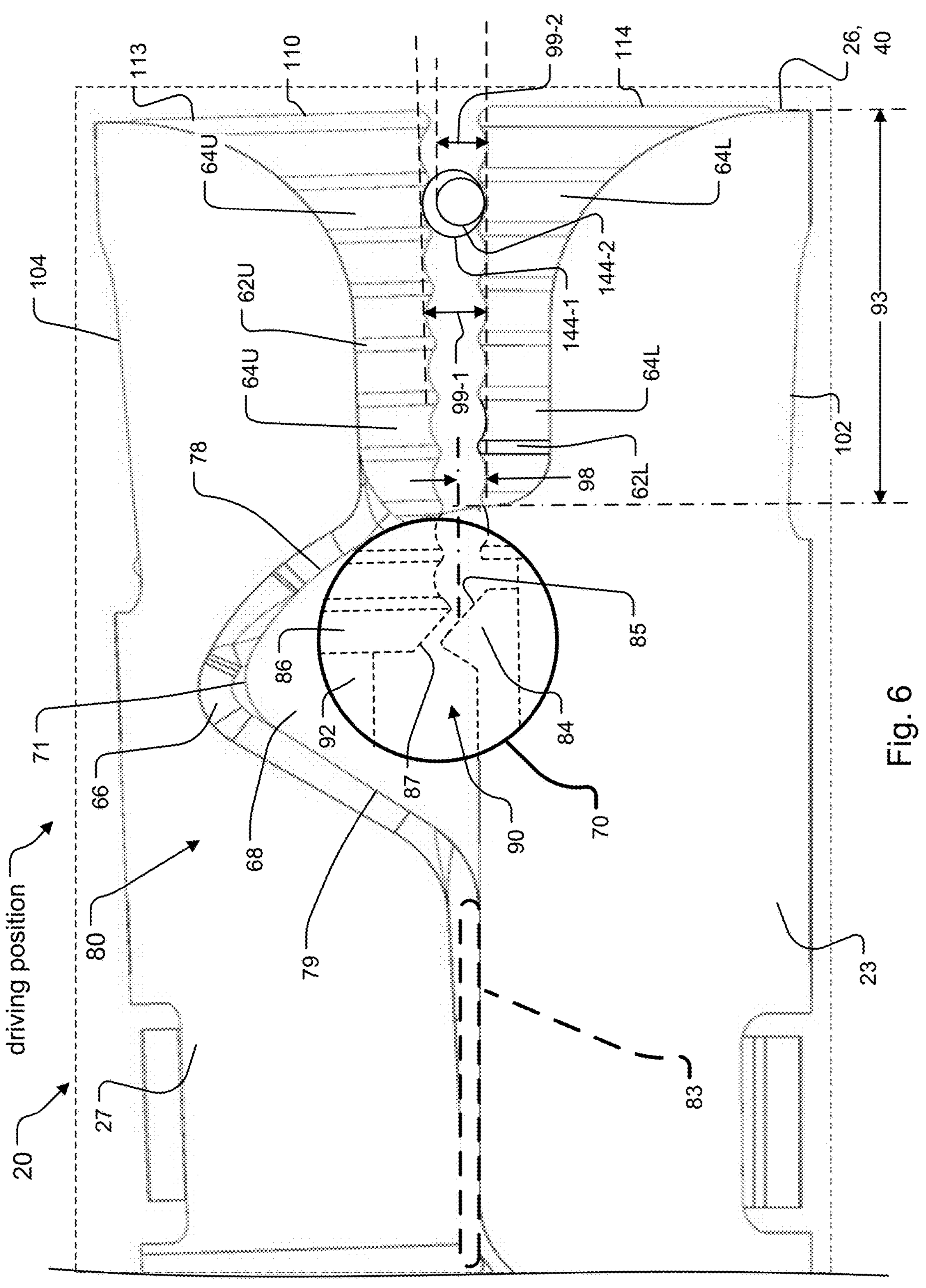
FIG. 6 is magnified side view of the inventive grip near the distal end of the needle driver, where the figure shows the grip in its driving position for driving a needle between rollers of the grip, and also shows the shifting feature within the grip.

FIG. 6 shows a side view of the grip 20 near the distal end 40 of the needle driver. The view shows more detail for the upper and lower rollers 110, 114 when either of two exemplary needles 144-1 and 144-2 are seated within the jaws/seated within opposing valleys 64U, 64L of the rollers 110, 114 and the grip 20 is in a driving position. The view also illustrates how common RB-1 and SH-1 type surgical needles can be grasped within the grasping portion 93 of the grip 20, specifically, within opposing valleys 64U, 64L of the upper and lower rollers 110, 114, and then be driven by the grip 20, without deployment of the shifting feature 90.

In the illustrated example, both an SH-1 needle 144-1 and an RB-1 needle 144-2 are shown within an opposing valley 64U, 64L of the upper and lower rollers 110, 114. The needles 144-1, 144-2 are shown such that their needle points are facing the viewer. A diameter 99-1 of the SH-1 needle and a diameter 99-2 of the RB-1 needle 144-2 are also shown.

Area 70 of the grip 20 shows the shifting feature 90 within the grip 20. The shifting feature 90 is shown in phantom. Here, the shifting feature 90 is not deployed. Specifically, the shifting feature 90 only begins to be deployed when the surgeon presses the lever 610, and the beveled edge 87 begins to contact the front face 85 of the canted stationary member 84. However, in the illustrated example, both of the needles 144-1, 144-2 are sufficiently large in diameter such that when the surgeon presses the lever 610, the opposing valleys 64L, 64U come into contact with either of the needles 144-1, 144-2 and the beveled edge 87 and the front face 85 do not come into contact with each other. Once the surgeon further presses the lever 610 to lock the lever, the grip 20 is placed into its driving position.

A shifting feature roller gap distance 98 of the grip 20 is defined as the distance between any opposing valleys 64U, 64L of the rollers 110, 114 when the surfaces 87, 85 of the shifting feature 90 begin to contact one another. A needle 144 with a diameter that is equal to or greater than the shifting feature roller gap distance 98 can be grasped and driven between the rollers 110, 114. At the same time, an object (such as a suture 146) with a diameter that is less than the shifting feature roller gap distance 98 will cause the surfaces 87, 85 to come into contact and begin deployment of the shifting feature 90. Because the diameters 99-1, 99-2 of the of the needles 144-1, 144-2 are both greater than the shifting feature roller gap distance 98, the grip 20 can grasp and drive the needles 144-1, 144-2 and the shifting feature 90 is not deployed.

Figure 7:
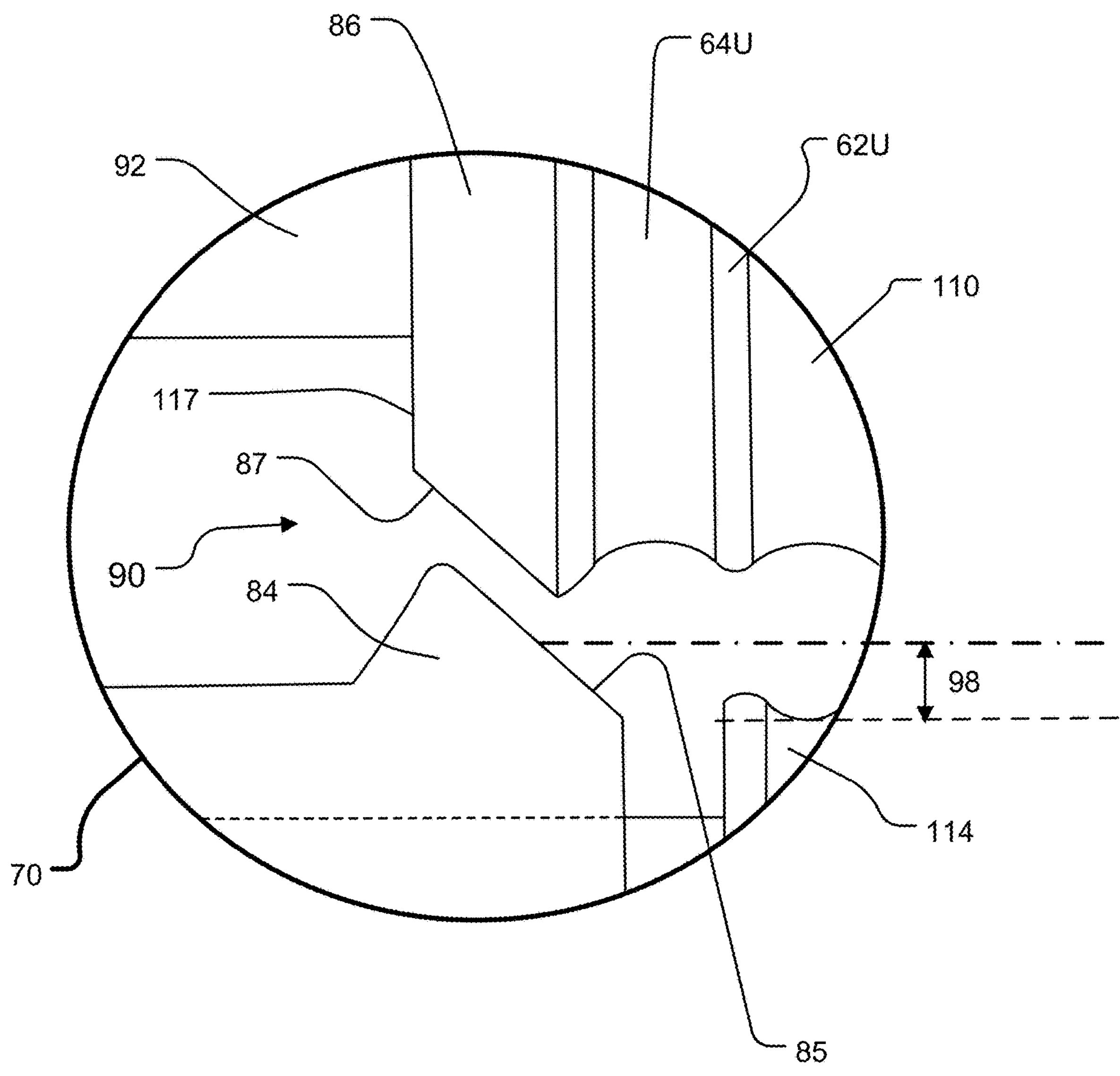
FIG. 7 is a magnified view of an area of the grip in FIG. 6 that includes the shifting feature, where the view shows that the shifting feature is not deployed when the grip is in its driving position.

FIG. 7 is an enlarged view of the area 70 in FIG. 6 and shows more detail for the shifting feature 90 than could be shown in FIG. 6. Here, the components of the shifting feature 90 in the area 70 are shown using solid lines rather than in phantom.

Figure 8:
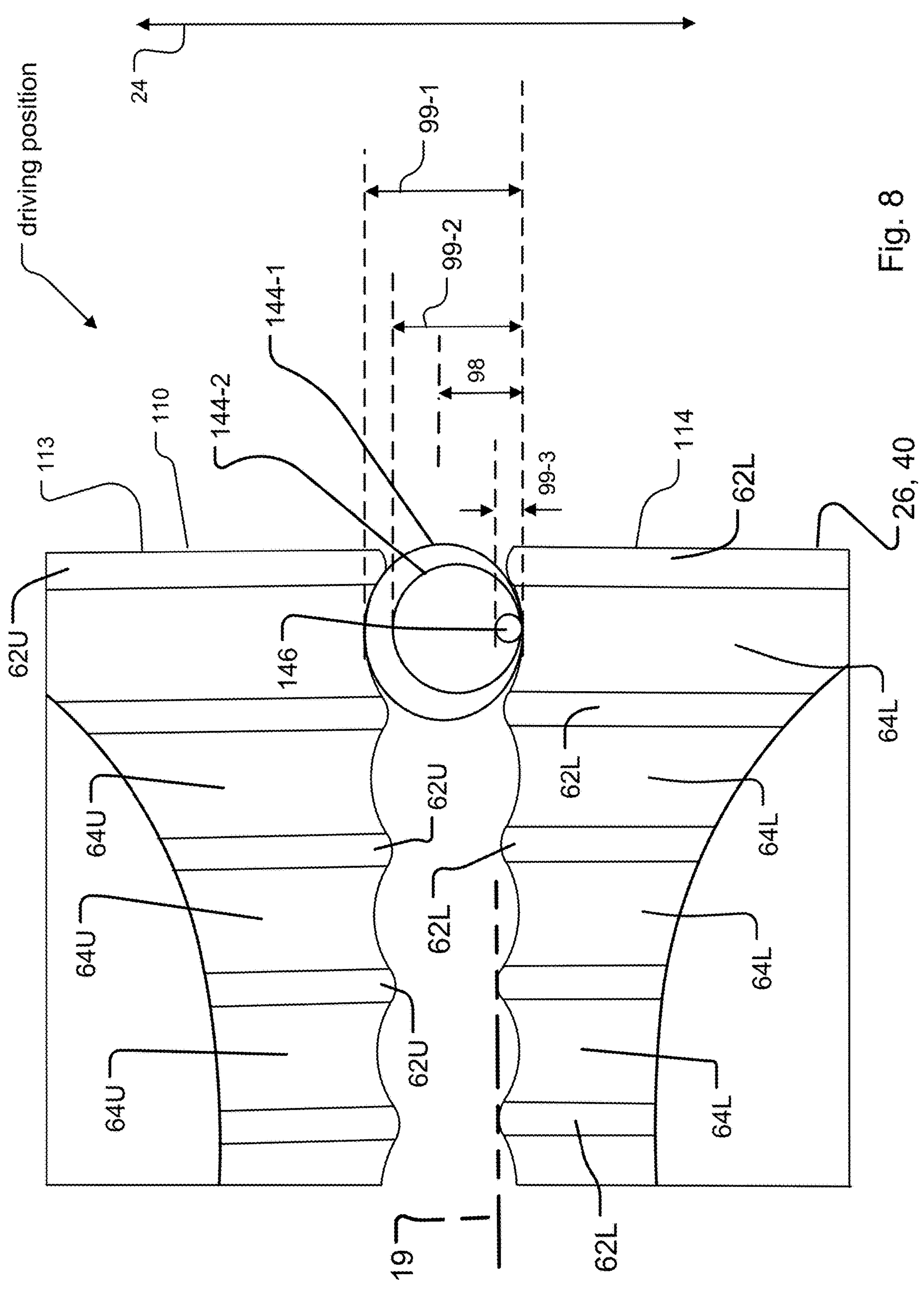
FIG. 8 is a further magnified view of FIG. 6 that focuses on the rollers near the distal end of the needle driver.

FIG. 8 shows a grip 20 as in FIG. 6. In the illustrated example, an SH-1 needle 144-1, an RB-1 needle 144-2, and a suture 146 are placed within an opposing valley 64U, 64L of the rollers 110, 114. The suture has a diameter 99-3. Here, the needles 144-1, 144-2 and the suture 146 are shown relative to one another and to the shifting feature roller gap distance 98.

In the illustrated example, the diameter 99-3 of the suture 146 is less than the shifting feature roller gap distance 98. As a result, the shifting feature 90 will begin deployment once the surgeon begins placing the lever 610 in its locked position.

Figure 9:
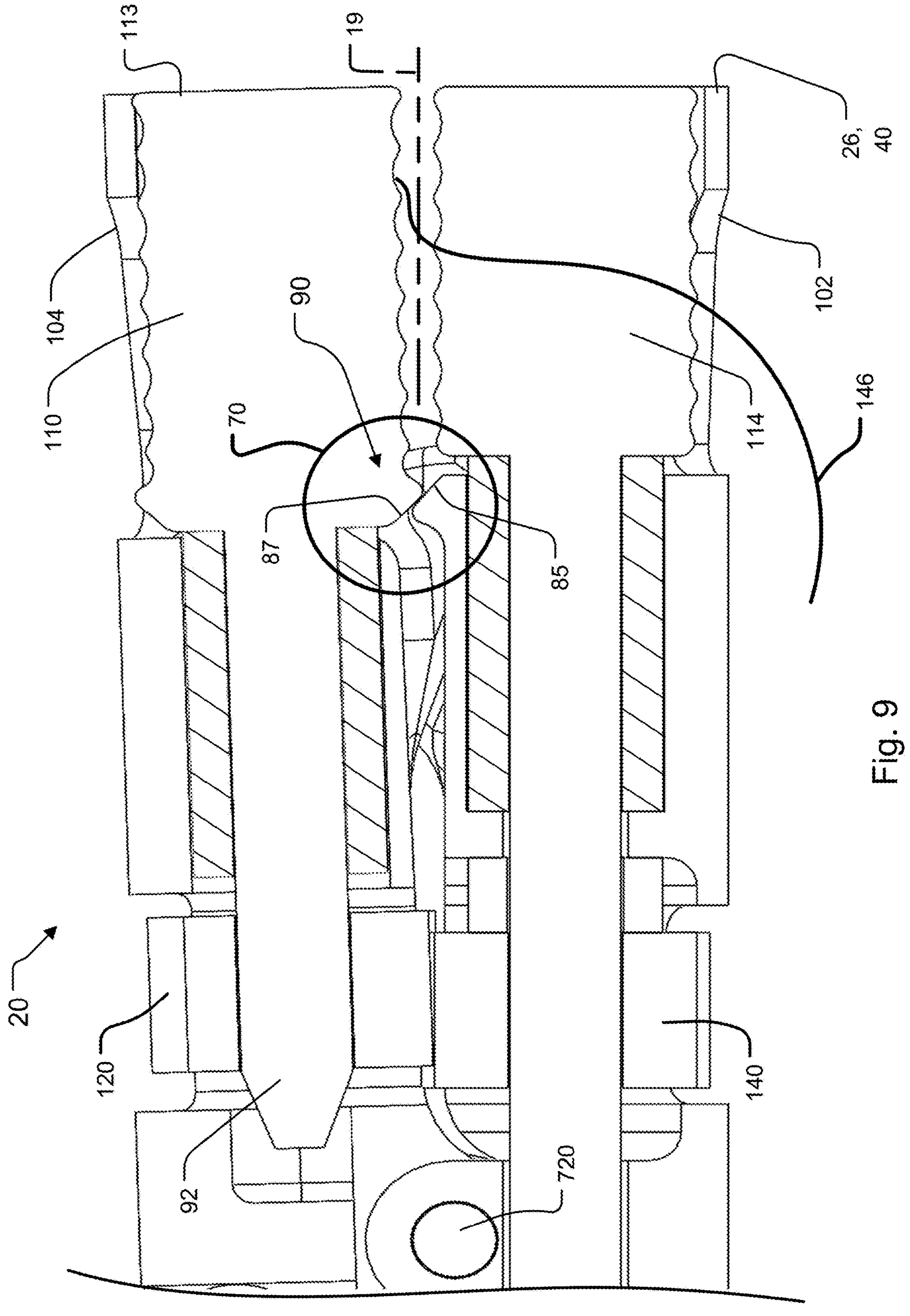
FIG. 9 is a side cross sectional view of the inventive grip, where the view shows the grip at the beginning of deployment of the shifting feature.

FIG. 9 shows the grip 20 as the shifting feature 90 begins deployment. In the illustrated example, only a suture 146 is located between the rollers 110, 114 when the surgeon presses the lever 610. The area 70 shows that beveled edge 87 of the beveled disc 86 of the upper roller 110 is in contact with the front face 85 of the canted stationary member 84.

Figure 10:
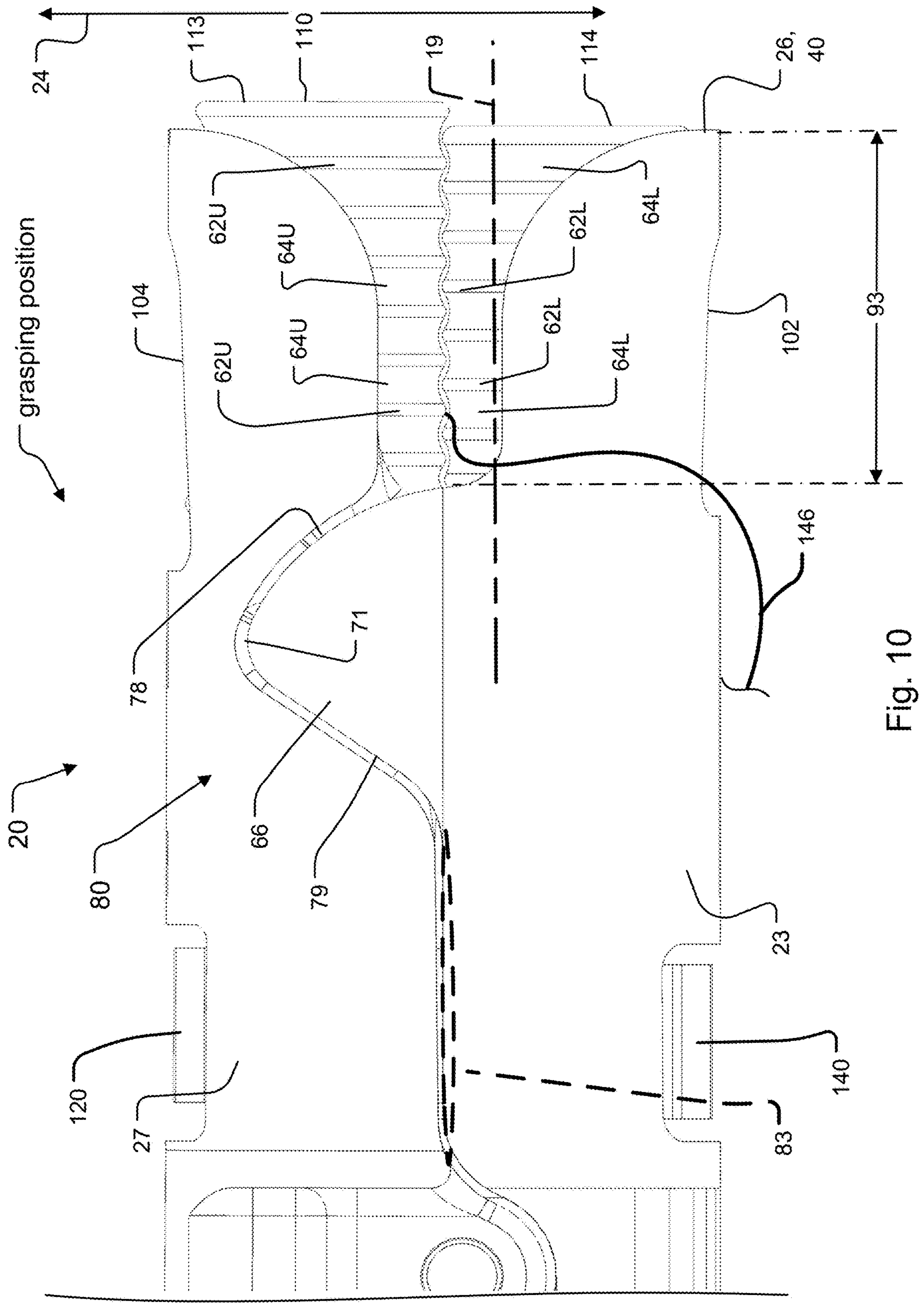
FIG. 10 is a magnified side view of the inventive grip near the distal end of the needle driver, where the figure shows the grip in its grasping position with the shifting feature fully deployed and a suture grasped between the rollers.

FIG. 10 shows the grip 20 after the surgeon completes locking of the lever 610 for the grip in FIG. 9. As a result, the shifting feature 90 is fully deployed to grasp the suture 146 between the rollers 110, 114. When the shifting feature 90 is fully deployed, the grip 20 is placed in a grasping position.

When the surgeon locks the lever 610, the beveled edge 87 of the beveled disc 86 of the upper roller 110 impinges upon the front surface 85 of the canted stationary member 84 under force. This moves the upper roller 110 in a distal direction along the longitudinal plane 19 towards the distal end 26 of the grip 40, while the lower roller 114 remains stationary in the longitudinal plane 19. Correspondingly, the peaks 62U of the upper roller 110 seat within the valleys 64L of the lower roller 114 until the rollers overlap/become asymmetrical. The suture 146 is thus firmly grasped between the rollers 110, 114. To release the suture 146 from the grasp of the rollers 110, 114, the surgeon merely releases the lever 610 from its locked position, and the grip 20 returns to its open position.

The upper roller 110 is generally loosely seated within the upper jaw 104 along the longitudinal plane 19. Once the shifting feature 90 is deployed, the upper roller 110 generally remains in its shifted position with respect to the lower roller 114. To place the upper roller 110 back in its default (non-shifted) position along the longitudinal plane 19, the surgeon can place the rollers 110, 114 around a needle 114 (with a diameter greater than the shifting feature roller gap distance 98) and place the lever 610 in its locking position. In response, the upper roller 110 shifts back in the proximal direction along the longitudinal plane 19 to is default position, the upper and lower valleys 64U, 64L of the rollers 110, 114 oppose one another again, and the grip is placed in its driving position.

In one implementation, the upper roller 110 is biased within the upper jaw 110 via a spring that keeps the upper roller 110 in its default, proximal-most position with respect to the longitudinal plane 19. This default position is useful when the grip 20 is either in its open position or its driving position. The spring tension or force is less than that imparted to the jaws 110, 114 during deployment of the shifting feature 90. In this way, the spring tension does not impede deployment of the shifting feature 90. Moreover, after the shifting feature 90 is deployed, when the surgeon unlocks the lever 610 to bring the grip 20 back to its open position, the spring tension causes the upper roller 110 to returns to its default position.

To again free the needle 144 and or/suture 146 completely from the rollers 110, 114, the surgeon moves the lever 610 to its open position furthest away from the housing 606, which places the grip 20 in its open position. The jaws 104, 102 are fully open, and the surgeon can move the grip 20 away from the needle 144 and or/suture 146.

The grip 20 with its shifting feature 90 enables the surgeon to drive needles and grasp sutures 146 in the grasping portion 93 of the grip 20 during a surgical or medical procedure. As compared to the existing grip 10, the improved grip 20 provides consistent and repeatable grasping of sutures 146 in the grasping portion 93 while also providing consistent and repeatable driving of needles 144 in the grasping portion 93. This saves procedure time and cost, reduces surgeon fatigue, and incurs less risk to the patient, both in tissue damage and chance of infection, and thus promotes improved patient outcomes.

Figure 11:
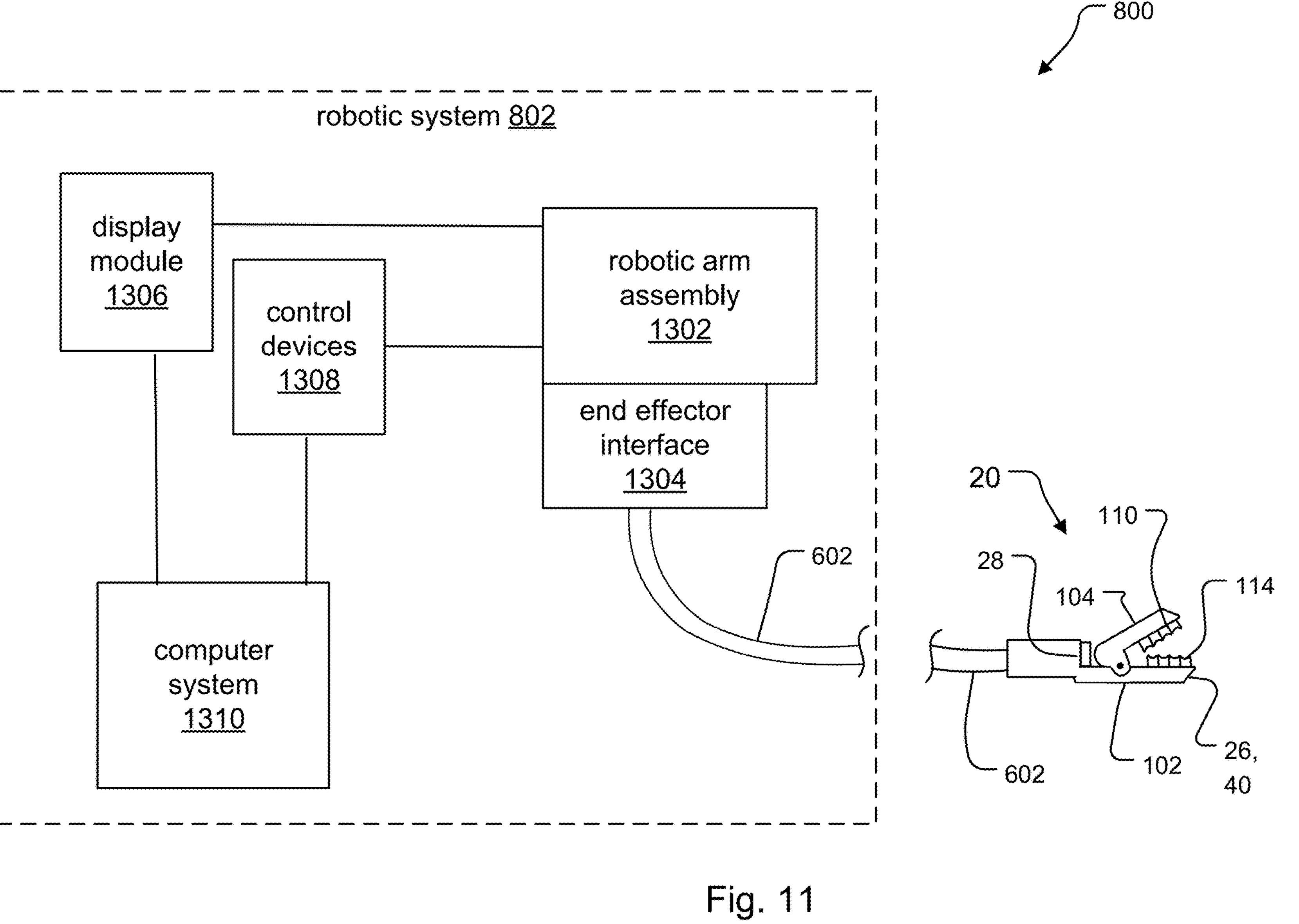
FIG. 11 is a schematic diagram of a robotic needle driver including the inventive grip, according to another embodiment, where the robotic needle driver includes a robotic system connected to the grip that operates as an actuating mechanism for manipulating the grip.

FIG. 11 shows an exemplary robotic needle driver 800. The robotic needle driver includes a robotic system 802 and the grip 20. The robotic system 802 includes a computer system 1310, a display module 1306, control devices 1308, a robotic arm assembly 1302 and an end effector interface 1304 of the robotic arm assembly 1302.

The grip 20 connects to the end effector interface 1304. The grip 20 can include any or all of the aspects and embodiments shown in FIGS. 3-10 and previously described herein above. The robotic system 802 operates as an actuating mechanism for manipulating the grip 20 to be in its open, closed and grasping positions.

The control devices 1308 enable an operator such as a surgeon to operate the robotic arm assembly 1302. The end effector interface 1304 might receive electrical signals from the robotic arm assembly 1302 and translate the signals to associated mechanical motion for the grip, and/or translate electromechanical motion from the robotic arm assembly 1302 to the grip 20. During surgery, the operator can view a targeted area of a patient undergoing surgery on the display module 1306.

In the illustrated example, the control devices 1308, robotic arm assembly 1302 and the end effector interface 1304 collectively provide all features of the handle 604 for manipulating the grip 20.

A material for one or more of the parts of the needle driver described herein is not limited and can include any material suitable for medical use. The material can be flexible, elastic, or resilient. The material can be suitable to be disinfected, sterilized, or sanitized, which can be with a hot steam, an autoclave, or others. For example, the material can include plastic, metal, rubber, shape memory, fabric, foam, or others.

While the inventions covered by the present disclosure have been particularly shown and described with references to preferred embodiments thereof, it will be understood by those skilled in the art that various changes in form and details may be made therein without departing from the scope of the invention(s) encompassed by the appended claims.

The invention claimed is:

1. A grip for a needle driver, the grip having a distal end located at a distal end of the needle driver, the grip comprising:

a first jaw and a second jaw, wherein the first jaw hosts a first roller and the second jaw hosts a second roller, and wherein the first roller includes a first groove pattern and the second roller includes a second groove pattern, and wherein the first jaw is pivotally connected to the second jaw via a pin located at a proximal end of the grip, the proximal end of the grip opposing its distal end;

a guard distributed across the first jaw and the second jaw, wherein the guard has a back edge that faces towards the proximal end of the grip and a front edge that faces towards the distal end of the needle driver;

a grasping portion that extends from the front edge of the guard to the distal end of the grip, wherein the groove patterns of the rollers are located within the grasping portion; and a non-grasping portion that extends from the back edge of the guard to the pin, wherein the guard includes:

a first flange that extends upward from a first side of the first jaw;

a second flange that extends upward from a second side of the first jaw wherein the first side of the first jaw is opposite to the second side of the first jaw in a longitudinal plane that extends from the proximal end of the grip to its distal end, and wherein the flanges each extend upward from a top surface of the first jaw to define the front edge of the guard, and then extend back downward to the top surface to define the back edge of the guard; and a first recess formed in a first side of the second jaw and a second recess formed in a second side of the second jaw, wherein the first side of the second jaw is opposite to the second side of the second jaw in the longitudinal plane;

wherein the first recess of the second jaw is configured to receive the first flange of the first jaw and the second recess of the second jaw is configured to receive the second flange of the first jaw, such that the first and second flanges seat within the first and second recesses, respectively, when the grip is either in a closed position or a grasping position, wherein each of the first and second flanges has a curved shape.

2. The grip of claim 1, wherein the guard is configured to prevent at least one of a needle or suture from entering the non-grasping portion from the front edge of the guard.

3. The grip of claim 1, wherein the grip is configured to drive a needle in the grasping portion, between the first groove pattern of the first roller and the second groove pattern of the second roller when the grip is in a driving position, and wherein the driving position is defined by:

peaks of the first groove pattern of the first roller being in alignment with peaks of the second groove pattern of the second roller; and valleys of the first groove pattern of the first roller being in alignment with valleys of the second groove pattern of the second roller.

4. The grip of claim 1, further comprising a shifting feature distributed across the first jaw and the second jaw that is configured to place the grip in the grasping position that enables a suture to be grasped between the rollers in the grasping portion.

5. A grip for a needle driver, the grip having a distal end located at a distal end of the needle driver, the grip comprising:

a first jaw and a second jaw, wherein the first jaw hosts a first roller and the second jaw hosts a second roller, and wherein the first roller includes a first groove pattern and the second roller includes a second groove pattern, and wherein the first jaw is pivotally connected to the second jaw via a pin located at a proximal end of the grip, the proximal end of the grip opposing its distal end;

a guard distributed across the first jaw and the second jaw, wherein the guard has a back edge that faces towards the proximal end of the grip and a front edge that faces towards the distal end of the needle driver;

a grasping portion that extends from the front edge of the guard to the distal end of the grip, wherein the groove patterns of the rollers are located within the grasping portion;

a non-grasping portion that extends from the back edge of the guard to the pin; and a shifting feature distributed across the first jaw and the second jaw that is configured to place the grip in a grasping position that enables a suture to be grasped between the rollers in the grasping portion, wherein the shifting feature moves the second roller in a longitudinal plane towards the distal end of the grip and away from the first roller while the first roller remains stationary in the longitudinal plane, until the second groove pattern of the second roller overlaps the first groove pattern of the first roller to place the grip in the grasping position.

6. The grip of claim 5, wherein the guard includes:

a first flange that extends upward from a first side of the first jaw;

a second flange that extends upward from a second side of the first jaw, wherein the first side of the first jaw is opposite to the second side of the first jaw in a longitudinal plane that extends from the proximal end of the grip to its distal end, and wherein the flanges each extend upward from a top surface of the first jaw to define the front edge of the guard, and then extend back downward to the top surface to define the back edge of the guard; and a first recess formed in a first side of the second jaw and a second recess formed in a second side of the second jaw, wherein the first side of the second jaw is opposite to the second side of the second jaw in the longitudinal plane;

wherein the first recess of the second jaw is configured to receive the first flange of the first jaw and the second recess of the second jaw is configured to receive the second flange of the first jaw, such that the first and second flanges seat within the first and second recesses, respectively, when the grip is either in a closed position or a grasping position.

7. The grip of claim 5, wherein each of the first and second groove patterns includes a plurality of peaks and valleys, and wherein prior to the grip being in its grasping position, the shifting feature begins to be deployed when a beveled edge of a beveled disc comes into contact with a front face of a canted stationary member to define a shifting feature roller gap distance between opposing valleys of the first and second groove patterns; and wherein when a suture having a diameter that is smaller than the shifting feature roller gap distance is located between the opposing valleys, the beveled edge of the beveled disc is increasingly configured to impinge upon the front face of the canted stationary member until the second groove pattern of the second roller overlaps the first groove pattern of the first roller to grasp the suture between the rollers.

8. The grip of claim 5, wherein the guard is configured to prevent at least one of a needle or suture from entering the non-grasping portion from the front edge of the guard.

9. The grip of claim 5, wherein the grip is configured to drive a needle in the grasping portion, between the first groove pattern of the first roller and the second groove pattern of the second roller when the grip is in a driving position, and wherein the driving position is defined by:

peaks of the first groove pattern of the first roller being in alignment with peaks of the second groove pattern of the second roller; and valleys of the first groove pattern of the first roller being in alignment with valleys of the second groove pattern of the second roller.

10. A grip for a needle driver, the grip having a distal end located at a distal end of the needle driver, the grip comprising:

a first jaw and a second jaw, wherein the first jaw hosts a first roller and the second jaw hosts a second roller, and wherein the first roller includes a first groove pattern and the second roller includes a second groove pattern, and wherein the first jaw is pivotally connected to the second jaw via a pin located at a proximal end of the grip, the proximal end of the grip opposing its distal end;

a guard distributed across the first jaw and the second jaw, wherein the guard has a back edge that faces towards the proximal end of the grip and a front edge that faces towards the distal end of the needle driver;

a grasping portion that extends from the front edge of the guard to the distal end of the grip, wherein the groove patterns of the rollers are located within the grasping portion;

a non-grasping portion that extends from the back edge of the guard to the pin;

a canted stationary member seated within the first jaw; and a beveled disc located at a back end of the second roller of the second jaw, wherein the back end of the second roller faces the proximal end of the grip, wherein upon impingement of the beveled disc on the canted stationary member, the second jaw is shifted distally relative to the first jaw.

11. The grip of claim 10, wherein the canted stationary member extends upward from a top surface of the first jaw, is canted towards the proximal end of the grip, and is canted in the proximal direction away from a vertical plane that is perpendicular to the top surface of the first jaw.

12. The grip of claim 10, wherein the beveled disc has a diameter larger than a diameter of the second groove pattern of the second roller.

13. The grip of claim 10, wherein the guard is configured to prevent at least one of a needle or suture from entering the non-grasping portion from the front edge of the guard.

14. The grip of claim 10, wherein the guard includes:

a first flange that extends upward from a first side of the first jaw;

a second flange that extends upward from a second side of the first jaw, wherein the first side of the first jaw is opposite to the second side of the first jaw in a longitudinal plane that extends from the proximal end of the grip to its distal end, and wherein the flanges each extend upward from a top surface of the first jaw to define the front edge of the guard, and then extend back downward to the top surface to define the back edge of the guard; and a first recess formed in a first side of the second jaw and a second recess formed in a second side of the second jaw, wherein the first side of the second jaw is opposite to the second side of the second jaw in the longitudinal plane;

wherein the first recess of the second jaw is configured to receive the first flange of the first jaw and the second recess of the second jaw is configured to receive the second flange of the first jaw, such that the first and second flanges seat within the first and second recesses, respectively, when the grip is either in a closed position or a grasping position.

15. The grip of claim 10, wherein the grip is configured to drive a needle in the grasping portion, between the first groove pattern of the first roller and the second groove pattern of the second roller when the grip is in a driving position, and wherein the driving position is defined by:

peaks of the first groove pattern of the first roller being in alignment with peaks of the second groove pattern of the second roller; and valleys of the first groove pattern of the first roller being in alignment with valleys of the second groove pattern of the second roller.

16. The grip of claim 10, further comprising a shifting feature distributed across the first jaw and the second jaw that is configured to place the grip in a grasping position that enables a suture to be grasped between the rollers in the grasping portion.

17. The grip of claim 16, wherein the shifting feature moves the second roller in a longitudinal plane towards the distal end of the grip and away from the first roller while the first roller remains stationary in the longitudinal plane, until the second groove pattern of the second roller overlaps the first groove pattern of the first roller to place the grip in the grasping position.

18. A needle driver comprising:

a grip located at a distal end of the needle driver, the grip including:

a first jaw and a second jaw, wherein the first jaw hosts a first roller and the second jaw hosts a second roller, and wherein the first roller includes a first groove pattern and the second roller includes a second groove pattern, and wherein the first jaw is pivotally connected to the second jaw via a pin located at a proximal end of the grip, the proximal end of the grip opposing its distal end;

a guard distributed across the first jaw and the second jaw, wherein the guard has a back edge that faces towards the proximal end of the grip and a front edge that faces towards the distal end of the needle driver;

a grasping portion that extends from the front edge of the guard to the distal end of the grip, wherein the groove patterns of the rollers are located within the grasping portion; and a non-grasping portion that extends from the back edge of the guard to the pin; and an actuating mechanism connected to the grip that is configured to enable the grip to drive a needle into tissue of a patient when the needle is located in the grasping portion, and to enable the grip to grasp at least one of a needle or a suture when the at least one of the needle or the suture is located in the grasping portion; and a shifting feature distributed across the first jaw and the second jaw that is configured to place the grip in a grasping position that enables a suture to be grasped between the rollers in the grasping portion, wherein the shifting feature moves the second roller in a longitudinal plane towards the distal end of the grip and away from the first roller while the first roller remains stationary in the longitudinal plane, until the second groove pattern of the second roller overlaps the first groove pattern of the first roller to place the grip in the grasping position.

19. The needle driver of claim 18, wherein the guard prevents the at least one of the needle or the suture from entering the non-grasping portion from the front edge of the guard.

20. The needle driver of claim 18, wherein the needle driver is a robotic needle driver that includes a robotic system, and wherein the robotic system is the actuating mechanism.

21. The needle driver of claim 18, wherein the actuating mechanism is a handle accommodated within a housing and includes at least one rotating shaft under control of the handle, and wherein the at least one rotating shaft connects to the grip.

22. A needle driver comprising:

a grip located at a distal end of the needle driver, the grip including:

a first jaw and a second jaw, wherein the first jaw hosts a first roller and the second jaw hosts a second roller, and wherein the first roller includes a first groove pattern and the second roller includes a second groove pattern, and wherein the first jaw is pivotally connected to the second jaw via a pin located at a proximal end of the grip, the proximal end of the grip opposing its distal end;

a guard distributed across the first jaw and the second jaw, wherein the guard has a back edge that faces towards the proximal end of the grip and a front edge that faces towards the distal end of the needle driver;

a grasping portion that extends from the front edge of the guard to the distal end of the grip, wherein the groove patterns of the rollers are located within the grasping portion; and a non-grasping portion that extends from the back edge of the guard to the pin; and an actuating mechanism connected to the grip that is configured to enable the grip to drive a needle into tissue of a patient when the needle is located in the grasping portion, and to enable the grip to grasp at least one of a needle or a suture when the at least one of the needle or the suture is located in the grasping portion;

a canted stationary member seated within the first jaw; and a beveled disc located at a back end of the second roller of the second jaw, wherein the back end of the second roller faces the proximal end of the grip, wherein upon impingement of the beveled disc on the canted stationary member, the second jaw is shifted distally relative to the first jaw.

23. The needle driver of claim 22, further comprising a shifting feature distributed across the first jaw and the second jaw that is configured to place the grip in a grasping position that enables a suture to be grasped between the rollers in the grasping portion.

24. The needle driver of claim 22, wherein the canted stationary member extends upward from a top surface of the first jaw, is canted towards the proximal end of the grip, and is canted in the proximal direction away from a vertical plane that is perpendicular to the top surface of the first jaw.

25. The needle driver of claim 22, wherein the guard prevents the at least one of the needle or the suture from entering the non-grasping portion from the front edge of the guard.

26. The needle driver of claim 22, wherein the needle driver is a robotic needle driver that includes a robotic system, and wherein the robotic system is the actuating mechanism.

27. The needle driver of claim 22, wherein the actuating mechanism is a handle accommodated within a housing and includes at least one rotating shaft under control of the handle, and wherein the at least one rotating shaft connects to the grip.

28. A needle driver comprising:

a grip located at a distal end of the needle driver, the grip including:

a first jaw and a second jaw, wherein the first jaw hosts a first roller and the second jaw hosts a second roller, and wherein the first roller includes a first groove pattern and the second roller includes a second groove pattern, and wherein the first jaw is pivotally connected to the second jaw via a pin located at a proximal end of the grip, the proximal end of the grip opposing its distal end;

a guard distributed across the first jaw and the second jaw, wherein the guard has a back edge that faces towards the proximal end of the grip and a front edge that faces towards the distal end of the needle driver;

a grasping portion that extends from the front edge of the guard to the distal end of the grip, wherein the groove patterns of the rollers are located within the grasping portion; and a non-grasping portion that extends from the back edge of the guard to the pin; and an actuating mechanism connected to the grip that is configured to enable the grip to drive a needle into tissue of a patient when the needle is located in the grasping portion, and to enable the grip to grasp at least one of a needle or a suture when the at least one of the needle or the suture is located in the grasping portion;

a shifting feature distributed across the first jaw and the second jaw that is configured to place the grip in a grasping position that enables a suture to be grasped between the rollers in the grasping portion;

a canted stationary member seated within the first jaw; and a beveled disc located at a back end of the second roller of the second jaw wherein the back end of the second roller faces the proximal end of the grip, wherein each of the first and second groove patterns includes a plurality of peaks and valleys, and wherein prior to the grip being in its grasping position, the shifting feature begins to be deployed when a beveled edge of the beveled disc comes into contact with a front face of the canted stationary member to define a shifting feature roller gap distance between opposing valleys of the first and second groove patterns; and wherein when a suture having a diameter that is smaller than the shifting feature roller gap distance is located between the opposing valleys, the beveled disc is increasingly configured to impinge upon the front face of the canted stationary member until the second groove pattern of the second roller overlaps the first groove pattern of the first roller to grasp the suture between the rollers.

29. The needle driver of claim 28, wherein the guard prevents the at least one of the needle or the suture from entering the non-grasping portion from the front edge of the guard.

30. The needle driver of claim 28, wherein the canted stationary member extends upward from a top surface of the first jaw, is canted towards the proximal end of the grip, and is canted in the proximal direction away from a vertical plane that is perpendicular to the top surface of the first jaw.

31. The needle driver of claim 28, wherein the needle driver is a robotic needle driver that includes a robotic system, and wherein the robotic system is the actuating mechanism.

32. The needle driver of claim 28, wherein the actuating mechanism is a handle accommodated within a housing and includes at least one rotating shaft under control of the handle, and wherein the at least one rotating shaft connects to the grip.

* * * * *